United States Patent
Ojeda et al.

(10) Patent No.: US 12,251,233 B2
(45) Date of Patent: *Mar. 18, 2025

(54) MULTIMODAL WEARABLE MEASUREMENT SYSTEMS AND METHODS

(71) Applicant: HI LLC, Los Angeles, CA (US)

(72) Inventors: Alejandro Ojeda, Culver City, CA (US); Ryan Field, Culver City, CA (US); Husam Katnani, Braintree, MA (US); Bruno Do Valle, Brighton, MA (US); Isai Olvera, South Portland, ME (US)

(73) Assignee: HI LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/521,771

(22) Filed: Nov. 28, 2023

(65) Prior Publication Data

US 2024/0090816 A1    Mar. 21, 2024

Related U.S. Application Data

(63) Continuation of application No. 17/176,309, filed on Feb. 16, 2021, now Pat. No. 11,883,181.

(Continued)

(51) Int. Cl.
*A61B 5/291* (2021.01)
*A61B 5/00* (2006.01)
*A61B 5/369* (2021.01)

(52) U.S. Cl.
CPC ............ *A61B 5/369* (2021.01); *A61B 5/0075* (2013.01); *A61B 5/291* (2021.01); *A61B 5/6803* (2013.01)

(58) Field of Classification Search
None
See application file for complete search history.

(56) References Cited

U.S. PATENT DOCUMENTS

| 4,321,930 A | 3/1982 | Jobsis et al. |
| 5,218,962 A | 6/1993 | Mannheimer et al. |

(Continued)

FOREIGN PATENT DOCUMENTS

| FR | 3011932 A1 | 4/2015 |
| JP | 2012125370 A | 1/2015 |

OTHER PUBLICATIONS

Alayed, et al., Characterization of a Time-Resolved Diffuse Optical Spectroscopy Prototype Using Low-Cost, Compact Single Photon Avalanche Detectors for Tissue Optics Applications, Sensors 2018, 18, 3680; doi:10.3390/s18113680, Oct. 29, 2018.

(Continued)

*Primary Examiner* — Aurelie H Tu
(74) *Attorney, Agent, or Firm* — ALG Intellectual Property, LLC

(57) ABSTRACT

An illustrative multimodal measurement system includes a wearable assembly configured to be worn by a user; and a module configured to be removably inserted into the wearable assembly and comprising: a housing, a printed circuit board (PCB) and a light guide assembly configured to emit light directed at a target within the user. The light guide assembly comprises: a lower light guide portion housed within the housing and having a proximal end attached to the PCB, a conductive spring member housed within the housing and comprising a coil positioned around an external surface of the lower light guide portion, and a conductive upper light guide portion connected to the lower light guide portion and configured to protrude from an upper surface of the housing and be in contact with a surface of a body of the user.

16 Claims, 21 Drawing Sheets

Related U.S. Application Data

(60) Provisional application No. 63/079,194, filed on Sep. 16, 2020, provisional application No. 63/006,824, filed on Apr. 8, 2020, provisional application No. 62/979,866, filed on Feb. 21, 2020.

(56) References Cited

U.S. PATENT DOCUMENTS

| | | |
|---|---|---|
| 5,853,370 A | 12/1998 | Chance et al. |
| 5,924,982 A | 7/1999 | Chin |
| 6,195,580 B1 | 2/2001 | Grable |
| 6,240,309 B1 | 5/2001 | Yamashita et al. |
| 6,291,842 B1 | 9/2001 | Nakayama |
| 6,384,663 B2 | 5/2002 | Cova et al. |
| 6,618,614 B1 | 9/2003 | Chance |
| 6,640,133 B2 | 10/2003 | Yamashita et al. |
| 6,683,294 B1 | 1/2004 | Herbert et al. |
| 7,356,365 B2 | 4/2008 | Schurman |
| 7,547,872 B2 | 6/2009 | Niclass et al. |
| 7,774,047 B2 | 8/2010 | Yamashita et al. |
| 7,888,973 B1 | 2/2011 | Rezzi et al. |
| 8,026,471 B2 | 9/2011 | Itzler |
| 8,078,250 B2 | 12/2011 | Chen et al. |
| 8,082,015 B2 | 12/2011 | Yodh et al. |
| 8,269,563 B2 | 9/2012 | Ballantyne |
| 8,518,029 B2 | 8/2013 | Birmingham et al. |
| 8,633,431 B2 | 1/2014 | Kim |
| 8,817,257 B2 | 8/2014 | Herve |
| 8,986,207 B2 | 3/2015 | Li et al. |
| 9,058,081 B2 | 6/2015 | Baxter |
| 9,076,707 B2 | 7/2015 | Harmon |
| 9,131,861 B2 | 9/2015 | Ince et al. |
| 9,316,735 B2 | 4/2016 | Baxter |
| 9,401,448 B2 | 7/2016 | Bienfang et al. |
| 9,419,635 B2 | 8/2016 | Kumar et al. |
| 9,442,201 B2 | 9/2016 | Schmand et al. |
| 9,529,079 B1 | 12/2016 | Droz et al. |
| 9,554,738 B1 | 1/2017 | Gulati et al. |
| 9,574,936 B2 | 2/2017 | Heinonen |
| 9,946,344 B2 | 4/2018 | Ayaz et al. |
| D817,553 S | 5/2018 | Aaskov et al. |
| 9,983,670 B2 | 5/2018 | Coleman et al. |
| D825,112 S | 8/2018 | Saez |
| 10,154,815 B2 | 12/2018 | Al-Ali et al. |
| 10,158,038 B1 | 12/2018 | Do et al. |
| 10,340,408 B1 | 7/2019 | Katnani et al. |
| 10,424,683 B1 | 9/2019 | Valle et al. |
| 10,515,993 B2 | 12/2019 | Field et al. |
| 10,541,660 B2 | 1/2020 | McKisson |
| 10,695,167 B2 | 6/2020 | Heugten et al. |
| 10,697,829 B2 | 6/2020 | Delic |
| 10,772,561 B2 | 9/2020 | Donaldson |
| 10,809,796 B2 | 10/2020 | Armstrong-Muntner et al. |
| 10,912,504 B2 | 2/2021 | Nakaji et al. |
| 11,006,876 B2 | 5/2021 | Johnson et al. |
| 11,006,878 B2 | 5/2021 | Johnson et al. |
| 11,137,283 B2 | 10/2021 | Balamurugan et al. |
| 11,213,245 B2 | 1/2022 | Horstmeyer et al. |
| 11,883,181 B2 * | 1/2024 | Ojeda .................. A61B 5/165 |
| 11,903,676 B2 | 2/2024 | Sorgenfrei et al. |
| 2002/0033454 A1 | 3/2002 | Cheng et al. |
| 2005/0059869 A1 | 3/2005 | Scharf et al. |
| 2006/0264722 A1 | 11/2006 | Hannula et al. |
| 2007/0083097 A1 | 4/2007 | Fujiwara et al. |
| 2008/0021341 A1 | 1/2008 | Harris et al. |
| 2009/0012402 A1 | 1/2009 | Mintz et al. |
| 2009/0054789 A1 * | 2/2009 | Kiguchi .............. A61B 5/0059 600/476 |
| 2010/0007413 A1 | 1/2010 | Herleikson et al. |
| 2010/0188649 A1 | 7/2010 | Prahl et al. |
| 2011/0208675 A1 | 8/2011 | Shoureshi et al. |
| 2012/0083673 A1 | 4/2012 | Al-Ali et al. |
| 2013/0153754 A1 | 6/2013 | Drader et al. |
| 2013/0300838 A1 | 11/2013 | Borowski et al. |
| 2013/0342835 A1 | 12/2013 | Blacksberg |
| 2014/0191115 A1 | 7/2014 | Webster et al. |
| 2014/0217264 A1 | 8/2014 | Shepard et al. |
| 2014/0275891 A1 | 9/2014 | Muehlemann et al. |
| 2015/0011848 A1 | 1/2015 | Ruchti et al. |
| 2015/0038811 A1 | 2/2015 | Asaka et al. |
| 2015/0038812 A1 | 2/2015 | Ayaz et al. |
| 2015/0041625 A1 | 2/2015 | Dutton et al. |
| 2015/0054111 A1 | 2/2015 | Niclass et al. |
| 2015/0077279 A1 | 3/2015 | Song et al. |
| 2015/0150505 A1 | 6/2015 | Kaskoun et al. |
| 2015/0157262 A1 | 6/2015 | Schuessler |
| 2015/0327777 A1 | 11/2015 | Kostic et al. |
| 2015/0364635 A1 | 12/2015 | Bodlovic et al. |
| 2016/0057369 A1 | 2/2016 | Wolfe et al. |
| 2016/0349368 A1 | 12/2016 | Stutz et al. |
| 2017/0030769 A1 | 2/2017 | Clemens et al. |
| 2017/0052065 A1 | 2/2017 | Sharma et al. |
| 2017/0176596 A1 | 6/2017 | Shpunt et al. |
| 2017/0179173 A1 | 6/2017 | Mandai et al. |
| 2017/0202518 A1 | 7/2017 | Furman et al. |
| 2017/0281086 A1 | 10/2017 | Donaldson |
| 2017/0338969 A1 | 11/2017 | Paul et al. |
| 2017/0363467 A1 | 12/2017 | Clemens et al. |
| 2017/0367650 A1 | 12/2017 | Wallois et al. |
| 2018/0014741 A1 | 1/2018 | Chou |
| 2018/0027196 A1 | 1/2018 | Yang et al. |
| 2018/0033751 A1 | 2/2018 | Ban et al. |
| 2018/0039053 A1 | 2/2018 | Kremer et al. |
| 2018/0070830 A1 | 3/2018 | Sutin et al. |
| 2018/0070831 A1 | 3/2018 | Sutin et al. |
| 2018/0089848 A1 | 3/2018 | Yang et al. |
| 2018/0090536 A1 | 3/2018 | Mandai et al. |
| 2018/0180473 A1 | 6/2018 | Clemens et al. |
| 2018/0192931 A1 | 7/2018 | Linden et al. |
| 2019/0025406 A1 | 1/2019 | Krelboim et al. |
| 2019/0113385 A1 | 4/2019 | Fukuchi |
| 2019/0175068 A1 | 6/2019 | Everdell |
| 2019/0239753 A1 | 8/2019 | Wentz |
| 2019/0355861 A1 | 11/2019 | Katnani et al. |
| 2019/0363210 A1 | 11/2019 | Valle et al. |
| 2019/0388018 A1 | 12/2019 | Horstmeyer et al. |
| 2020/0022581 A1 | 1/2020 | Vanegas et al. |
| 2020/0060542 A1 | 2/2020 | Alford et al. |
| 2020/0116838 A1 | 4/2020 | Erdogan et al. |
| 2020/0196932 A1 | 6/2020 | Johnson et al. |
| 2020/0253479 A1 | 8/2020 | Nurmikko |
| 2020/0315510 A1 | 10/2020 | Johnson et al. |
| 2020/0337624 A1 | 10/2020 | Johnson et al. |
| 2020/0379095 A1 | 12/2020 | Kappel et al. |
| 2020/0390358 A1 | 12/2020 | Johnson et al. |
| 2021/0186138 A1 | 6/2021 | Bartels et al. |
| 2021/0223098 A1 | 7/2021 | Ledvina et al. |

OTHER PUBLICATIONS

Ban, et al., Kernel Flow: a high channel count scalable TD-fNIRS system, https://www.spiedigitallibrary.org/conference-proceedings-of-spie Proc. of SPIE vol. 11663, 116630B doi: 10.1117/12.2582888, Mar. 5, 2021.

Ban, et al., Kernel Flow: a high channel count scalable time-domain functional near-infrared spectroscopy system, https://www.spiedigitallibrary.org/journals/Journal-of-Biomedical-Optics on Jan. 18, 2022.

Contini, et al., Photon migration through a turbid slab described by a model based on diffusion approximation. I. Theory, Appl. Opt. 36(19), 4587 (1997).

Di Sieno, et al., Probe-hosted large area silicon photomultiplier and high-throughput timing electronics for enhanced performance time-domain functional near-infrared spectroscopy, Biomed. Opt. Express 11(11), 6389 (2020).

Fishburn, et al., Temporal Derivative Distribution Repair (TDDR): A motion correction method for fNIRS, Neuroimage. Jan. 1, 2019; 184: 171-179. doi:10.1016/j.neuroimage.2018.09.025.

Huppert, et al., HomER: a review of time-series analysis methods for near-infrared spectroscopy of the brain, Appl. Opt. 48(10), D280 (2009).

(56) References Cited

OTHER PUBLICATIONS

Kienle, et al., Improved solutions of the steady-state and the time-resolved diffusion equations for reflectance from a semi-infinite turbid medium, J. Opt. Soc. Am. A 14(1), 246 (1997).
Konugolu, et al., Broadband (600-1350 nm) Time-Resolved Diffuse Optical Spectrometer for Clinical Use, IEEE Journal of Selected Topics in Quantum Electronics, vol. 22, No. 3, May/Jun. 2016.
Lacerenza, et al., Wearable and wireless time-domain near-infrared spectroscopy system for brain and muscle hemodynamic monitoring, Biomed. Opt. Express 11(10), 5934 (2020).
Lange, et al., Clinical Brain Monitoring with Time Domain NIRS: A Review and Future Perspectives, Applied Sciences 9(8), 1612 (2019).
Lange, et al., Maestros: A Multiwavelength Time-Domain NIRS System to Monitor Changes in Oxygenation and Oxidation State of Cytochrome-C-Oxidase, IEEE J. Select. Topics Quantum Electron. 25(1), 1-12 (2019).
Martelli, et al., Optimal estimation reconstruction of the optical properties of a two-layered tissue phantom from time-resolved single-distance measurements, Journal of Biomedical Optics 20(11), 115001 (Nov. 2015).
Mora, et al., Fast silicon photomultiplier improves signal harvesting and reduces complexity in time-domain diffuse optics, Opt. Express 23(11), 13937 (2015).
Pifferi, et al., Performance assessment of photon migration instruments: the MEDPHOT protocol, Applied Optics, 44 (11), 2104-2114, 2005.
Prahl, Optical Absorption of Hemoglobin, http://omlc.ogi.edu/spectra/hemoglobin/index.html, 1999.
Re, et al., Multi-channel medical device for time domain functional near infrared spectroscopy based on wavelength space multiplexing, Biomed. Opt. Express 4(10), 2231 (2013).
Renna, et al., Eight-Wavelength, Dual Detection Channel Instrument for Near-Infrared Time-Resolved Diffuse Optical Spectroscopy, IEEE J. Select. Topics Quantum Electron. 25(1), 1-11 (2019).
Torricelli, et al., Time domain functional NIRS imaging for human brain mapping, NeuroImage 85, 28-50 (2014).
Wabnitz, et al., Depth-selective data analysis for time-domain fNIRS: moments vs. time windows, Biomed. Opt. Express 11(8), 4224 (2020).
Wabnitz, et al., Performance assessment of time-domain optical brain imagers, part 1: basic instrumental performance protocol, Journal of Biomedical Optics 19(8), 086010 (Aug. 2014).
Wabnitz, et al., Performance assessment of time-domain optical brain imagers, part 2: nEUROPt protocol, Journal of Biomedical Optics 19(8), 086012 (Aug. 2014).
Wojtkiewicz, et al., Self-calibrating time-resolved near infrared spectroscopy, Biomed. Opt. Express 10(5), 2657 (2019).
Zucchelli, et al., Method for the discrimination of superficial and deep absorption variations by time domain fNIRS, 2013 OSA Dec. 1, 2013 | vol. 4, No. 12 | DOI: 10.1364/BOE.4.002893 | Biomedical Optics Express 2893, 2013.
"What are the advantages of multiplexing," Blog, FiberWDM, Mar. 28, 2023. Retrieved on May 9, 2014 from https://www.fiberwdm.com/blog/what-are-the-advantages-of-multiplexing_b101.
Blair, Seraphine. "Multiplexing in modern communication: what it is & advantages," Blog, JAK Electronics, Mar. 12, 2024. Retrieved on May 9, 2024 from https://www.jakelectronics.com/blog/multiplexing.
Nandalal, et al., "Multiplexing," IntechOpen, Sep. 4, 2019. Retrieved on May 9, 2014 from https://www.jakelectronics.com/blog/multiplexing.

* cited by examiner

MULTIMODAL WEARABLE MEASUREMENT SYSTEMS AND METHODS

RELATED APPLICATIONS

The present application is a continuation of U.S. patent application Ser. No. 17/176,309, filed on Feb. 16, 2021, which claims priority under 35 U.S.C. § 119(e) to U.S. Provisional Patent Application No. 63/079,194, filed on Sep. 16, 2020, and to U.S. Provisional Patent Application No. 63/006,824, filed on Apr. 8, 2020, and to U.S. Provisional Patent Application No. 62/979,866, filed on Feb. 21, 2020. These applications are incorporated herein by reference in their respective entireties.

BACKGROUND INFORMATION

Detecting neural activity in the brain (or any other turbid medium) is useful for medical diagnostics, imaging, neuroengineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
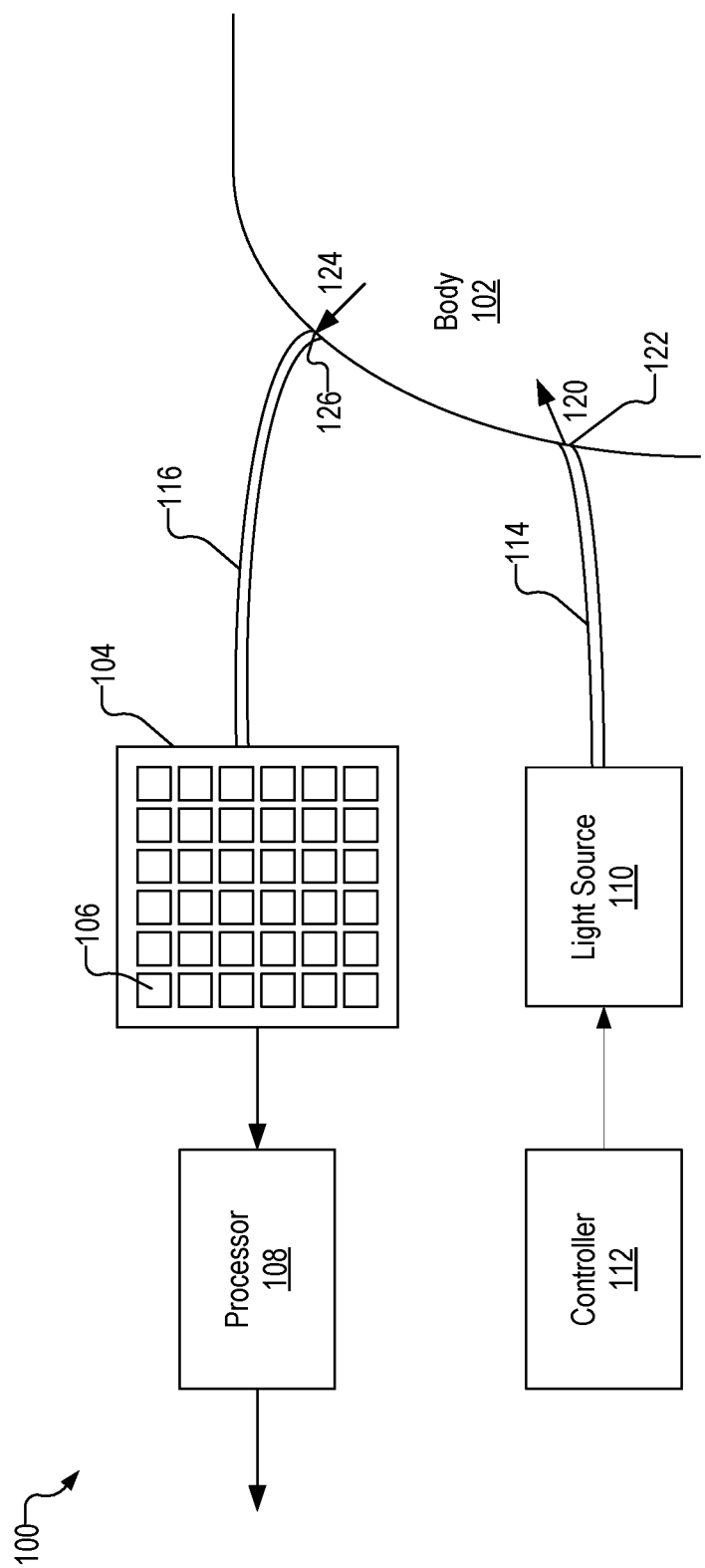
FIG. 1 illustrates an exemplary optical measurement system.

Functional near infrared spectroscopy (fNIRS) is a brain imaging modality that allows the indirect inference of cortical responses (a proxy for neural activity) by measuring the hemodynamic response of the brain tissue in different cortical regions. Compared to function magnetic resonance imaging (fMRI), another imaging modality based on the hemodynamic response, fNIRS can be mobile and low cost, allowing the large-scale use of imaging technology to study the brain, either within a tightly constrained environment of a scientific lab or in real-world scenarios, where subjects interact freely with their environment. One disadvantage of fNIRS, however, is that it is slow compared to the temporal dynamics of the current dipoles produced by neurons firing in the cortex. Another drawback of fNIRS is that there is no unique inverse mapping (ill-posed problem) from the measurements onto the consumption of oxyhemoglobin (OHb) and deoxyhemoglobin (HHb) molecules in different parts of the cortex. One way to solve this inverse problem is to introduce mathematical constraints into the reconstruction algorithm. Furthermore, fNIRS source reconstruction is typically performed offline using standard inverse solvers not optimized for this type of data.

Another low-cost and mobile brain imaging modality is electroencephalogram (EEG). Compared with fNIRS, EEG devices have a better temporal resolution because they use scalp sensors (e.g., electrodes) to measure the macroscopic electrical activity generated by clusters of cortical neurons that synchronize in space and time. Like fNIRS, the inverse mapping from EEG voltage sensors onto cortical current dipoles is not unique, therefore, to solve this inverse problem constraints are also needed. As such, fNIRS and EEG data fusion is attractive for brain imaging because each modality can complement each other by bringing data-driven constraints into an inverse mapping algorithm in which each constraint is enforced at the right spatiotemporal scales.

Accordingly, multimodal wearable measurement systems that include both optical and electrical activity measurement components are described herein. An exemplary multimodal measurement system includes a wearable assembly configured to be worn by a user and comprising a plurality of light sources each configured to emit light directed at a target within the user, a plurality of detectors configured to detect arrival times for photons of the light after the light is scattered by the target, and a plurality of electrodes configured to be external to the user and detect electrical activity of the target. In some examples, the multimodal measurement system further includes a processing unit configured to generate optical measurement data based on the arrival times detected by the detectors and electrical measurement data based on the electrical activity detected by the electrodes. The processing unit may be further configured to process the optical measurement data and the electrical measurement data (e.g., in real time during operation of the detectors and electrodes) in accordance with a data fusion heuristic to generate an estimate of cortical source activity and/or otherwise determine one or more other physiological characteristics of a user.

The systems and methods described herein may provide various benefits. For example, the systems and methods described herein may be optimized for brain tomography based on a computationally efficient fusion of optical measurement data (e.g., fNIRS data) and electrical measurement data (e.g., EEG data). This fusion method may benefit brain mapping algorithms by providing data-driven spatiotemporal constraints at different temporal scales. In particular, the systems and methods described herein may allow for computationally efficient real-time imaging. This technology has the potential to improve basic neuro-scientific research as well as the development of imaging-based translational neurotechnologies, such as brain-computer interfaces (BCIs) and continuous brain monitoring.

These and other advantages and benefits of the present systems and methods are described more fully herein and/or will be made apparent in the description herein.

FIG. 1 shows an exemplary optical measurement system 100 configured to perform an optical measurement operation with respect to a body 102. Optical measurement system 100 may, in some examples, be portable and/or wearable by a user.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain digital optical tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light guides, as described more fully herein). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diode (sLEDs), vertical-cavity surface-emitting lasers (VCSELs), titanium sapphire lasers, a micro light emitting diodes (mLEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a light guide, a waveguide, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., tissue, blood flow, etc.) in body 102. Example embodiments of accumulated outputs are described herein.

Figure 2:
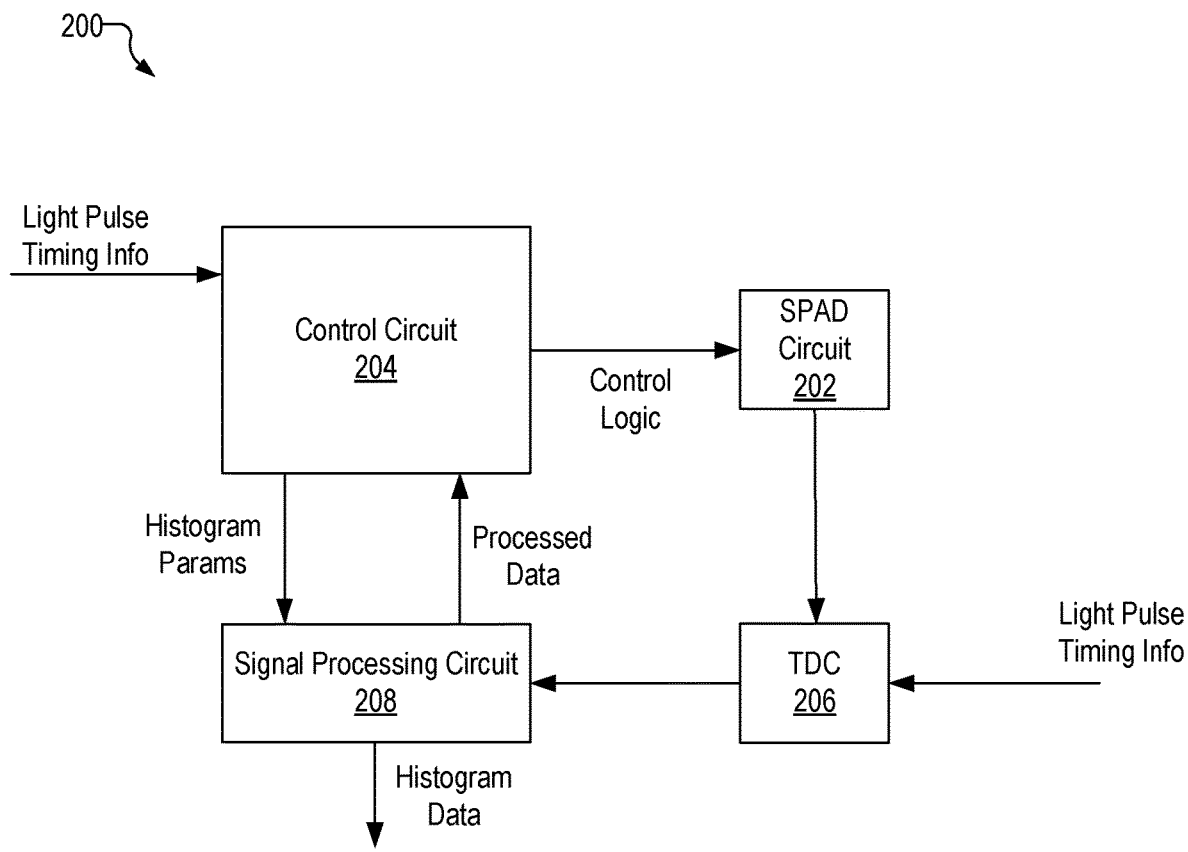
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
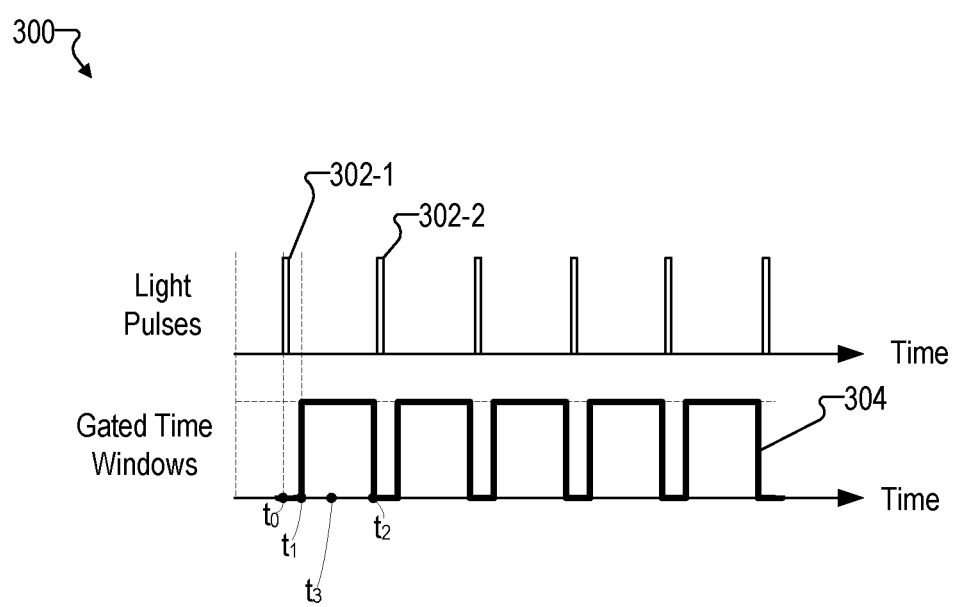
FIG. 3 illustrates an exemplary timing diagram for performing an optical measurement operation using an optical measurement system.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

Figure 4:
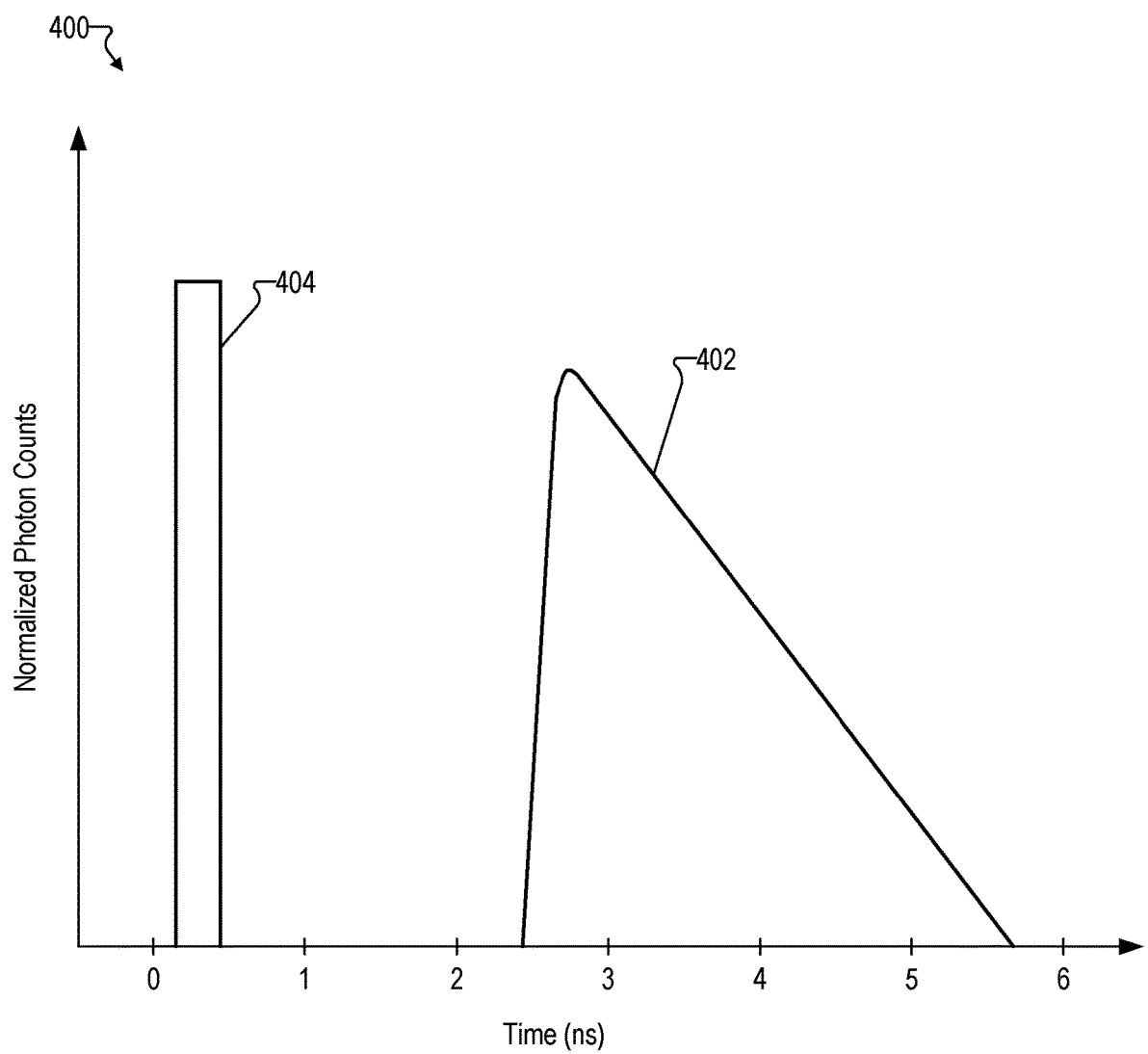
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological (e.g., neural) activity.

Optical measurement system 100 may be implemented by or included in any suitable device(s). For example, optical measurement system 100 may be included in a non-wearable device (e.g., a medical device and/or consumer device that is placed near the head or other body part of a user to perform one or more diagnostic, imaging, and/or consumer-related operations). Optical measurement system 100 may alternatively be included, in whole or in part, in a subassembly enclosure of a wearable invasive device (e.g., an implantable medical device for brain recording and imaging).

Alternatively, optical measurement system 100 may be included, in whole or in part, in a non-invasive wearable device that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
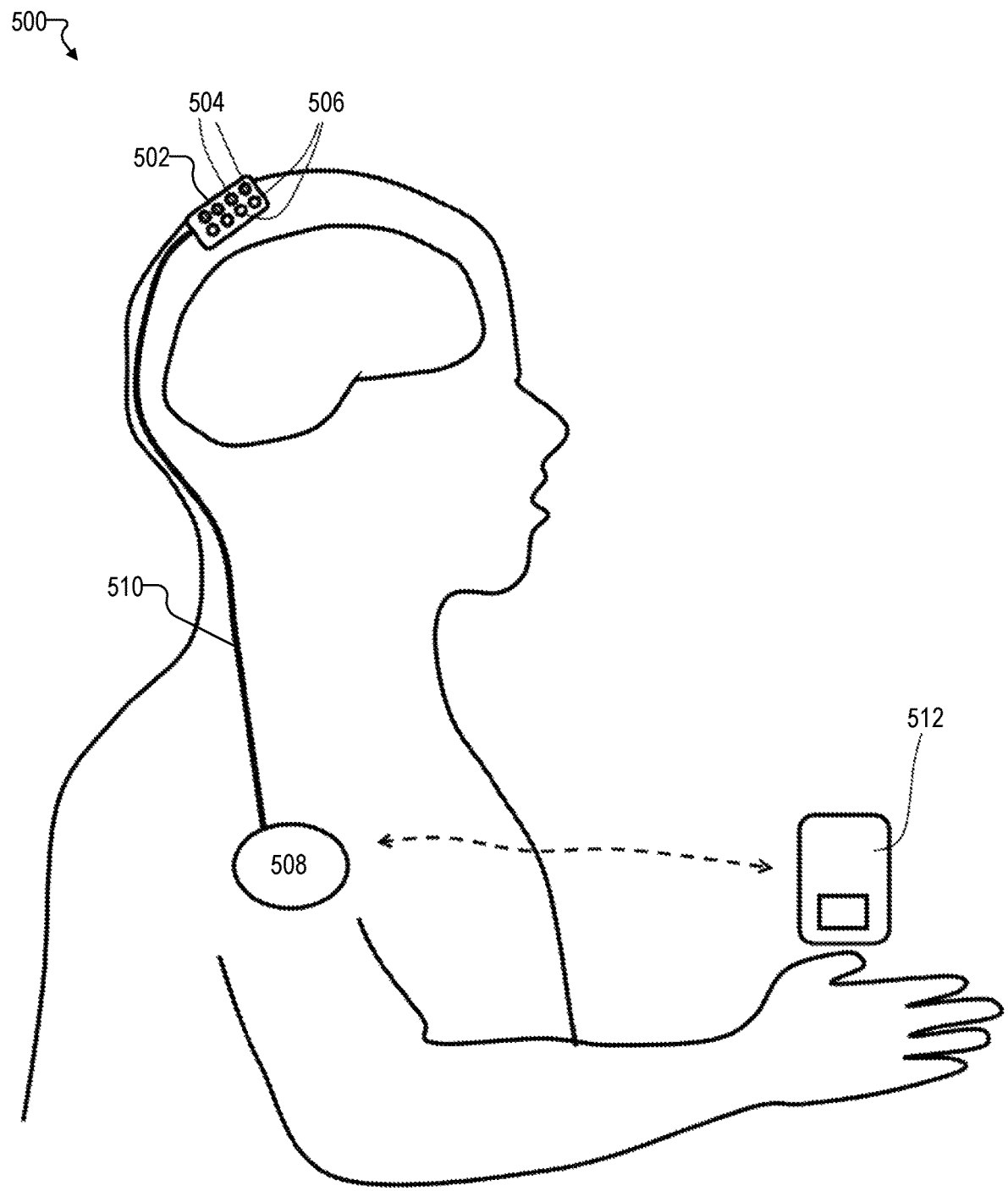
FIG. 5 illustrates an exemplary non-invasive wearable brain interface system.

To illustrate, FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to and/or worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described below in more detail and in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and/or for transforming photodetector measurements into an intensity value that represents an optical property of a target within the brain. Brain interface system 500 allows optical detection of deep anatomical locations beyond skin and bone (e.g., skull) by extracting data from photons originating from light sources 506 and emitted to a target location within the user's brain, in contrast to conventional imaging systems and methods (e.g., optical coherence tomography (OCT), continuous wave near infrared spectroscopy (CW-NIRS)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506. In some examples, processor 508 is implemented by or similar to processor 108 and/or controller 112.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). In some examples, remote processor 512 is implemented by or similar to processor 108 and/or controller 112.

Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and/or in another wearable or non-wearable device and coupled to head mountable component 502 through an optical connection.

In some alternative embodiments, head mountable component 502 does not include individual detectors 504. Instead, one or more detectors configured to detect the scattered light from the target may be included elsewhere in brain interface system 500. For example, a detector may be included in processor 508 and/or in another wearable or non-wearable device and coupled to head mountable component 502 through an optical connection.

Figure 6:
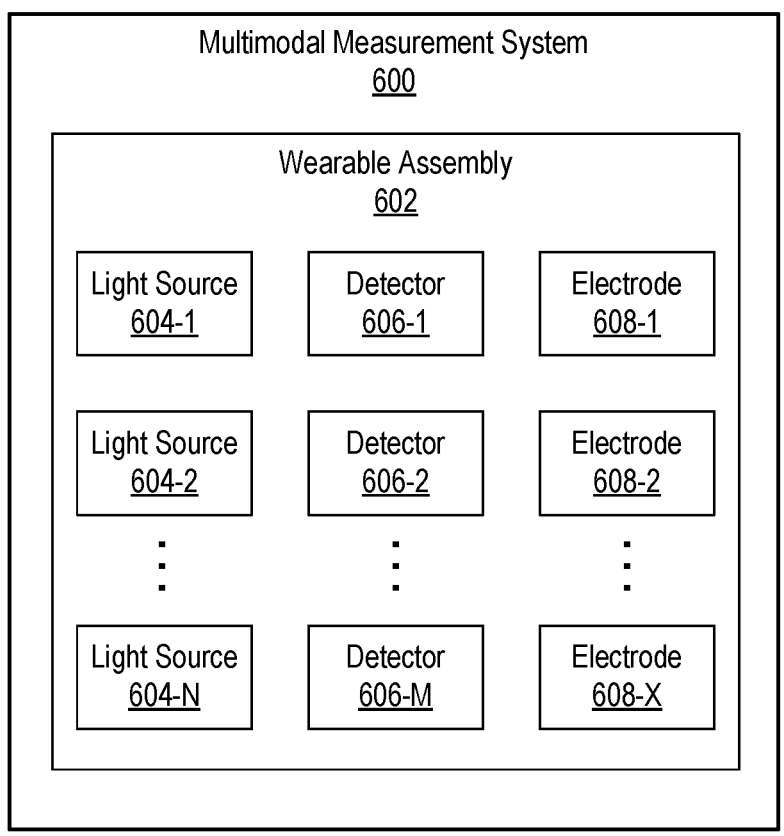
FIG. 6 shows an exemplary multimodal measurement system.

FIG. 6 shows an exemplary multimodal measurement system 600 in accordance with the principles described herein. Multimodal measurement system 600 may at least partially implement optical measurement system 100 and, as shown, includes a wearable assembly 602, which includes N light sources 604 (e.g., light sources 604-1 through 604-N), M detectors 606 (e.g., detectors 606-1 through 606-M), and X electrodes (e.g., electrodes 608-1 through 608-X). Multimodal measurement system 600 may include any of the other components of optical measurement system 100 as may serve a particular implementation. N, M, and X may each be any suitable value (i.e., there may be any number of light sources 604, any number of detectors 606, and any number of electrodes 608 included in multimodal measurement system 600 as may serve a particular implementation).

Light sources 604 are each configured to emit light (e.g., a sequence of light pulses) and may be implemented by any of the light sources described herein.

Detectors 606 may each be configured to detect arrival times for photons of the light emitted by one or more light sources 604 after the light is scattered by the target. For example, a detector 606 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector). Detectors 606 may be implemented by any of the detectors described herein.

Electrodes 608 may be configured to detect electrical activity within a target (e.g., the brain). Such electrical activity may include EEG activity and/or any other suitable type of electrical activity as may serve a particular implementation. In some examples, electrodes 608 are all conductively coupled to one another to create a single channel that may be used to detect electrical activity. Alternatively, at least one electrode included in electrodes 608 is conductively isolated from a remaining number of electrodes included in electrodes 608 to create at least two channels that may be used to detect electrical activity.

Wearable assembly 602 may be implemented by any of the wearable devices, modular assemblies, and/or wearable units described herein. For example, wearable assembly 602 may be implemented by a wearable device (e.g., headgear) configured to be worn on a user's head. Wearable assembly 602 may additionally or alternatively be configured to be worn on any other part of a user's body.

Multimodal measurement system 600 may be modular in that one or more components of multimodal measurement system 600 may be removed, changed out, or otherwise modified as may serve a particular implementation. Additionally or alternatively, multimodal measurement system 600 may be modular such that one or more components of multimodal measurement system 600 may be housed in a separate housing (e.g., module) and/or may be movable relative to other components. Exemplary modular multimodal measurement systems are described in more detail in U.S. Provisional Patent Application No. 63/081,754, filed Sep. 22, 2020, U.S. Provisional Patent Application No. 63/038,459, filed Jun. 12, 2020, U.S. Provisional Patent Application No. 63/038,468, filed Jun. 12, 2020, U.S. Provisional Patent Application No. 63/038,481, filed Jun. 12, 2020, and U.S. Provisional Patent Application No. 63/064,688, filed Aug. 12, 2020, which applications are incorporated herein by reference in their respective entireties.

To illustrate, various modular assemblies that may implement multimodal measurement system 600 are described in connection with FIGS. 7-9. The modular assemblies described herein are merely illustrative of the many different implementations of multimodal measurement system 600 that may be realized in accordance with the principles described herein. Each of the modular assemblies described herein may include one or more modules and may be worn on the head or any other suitable body part of the user.

Figure 7:
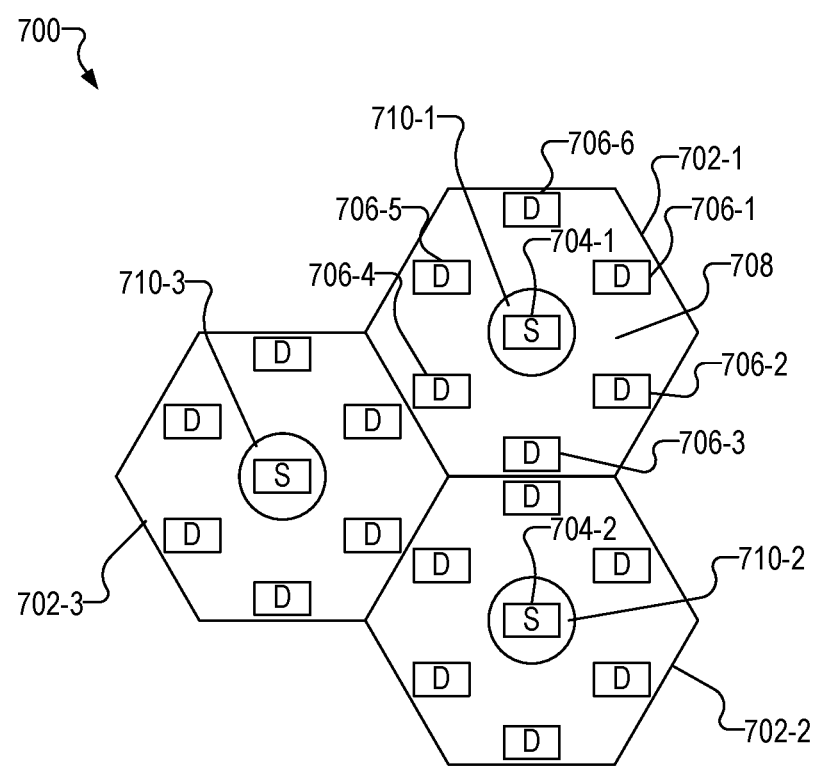
FIGS. 7-9 illustrates various modular assemblies.
Figure 8A:
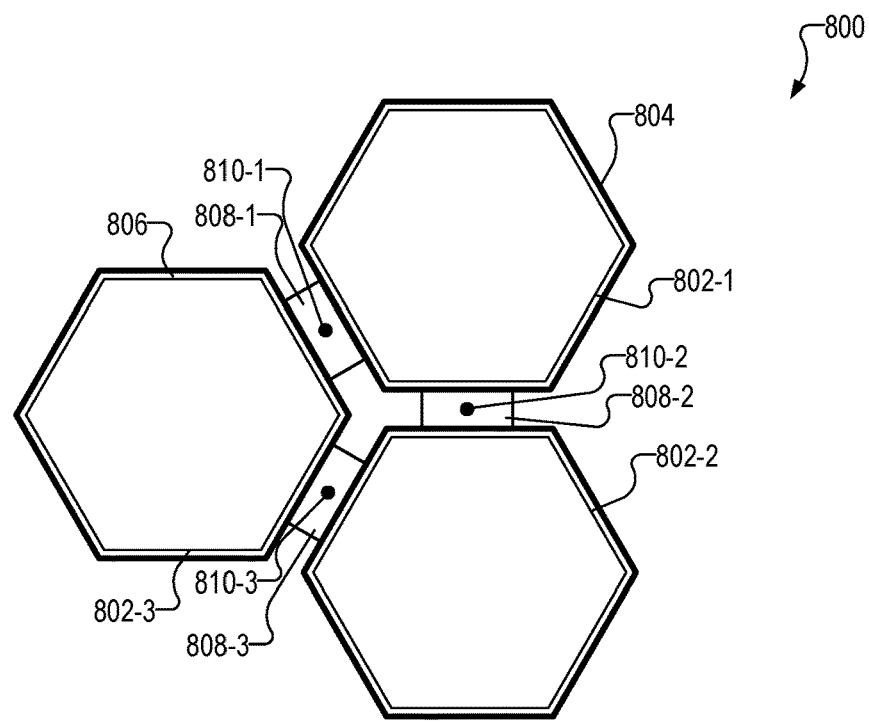
Figure 8B:
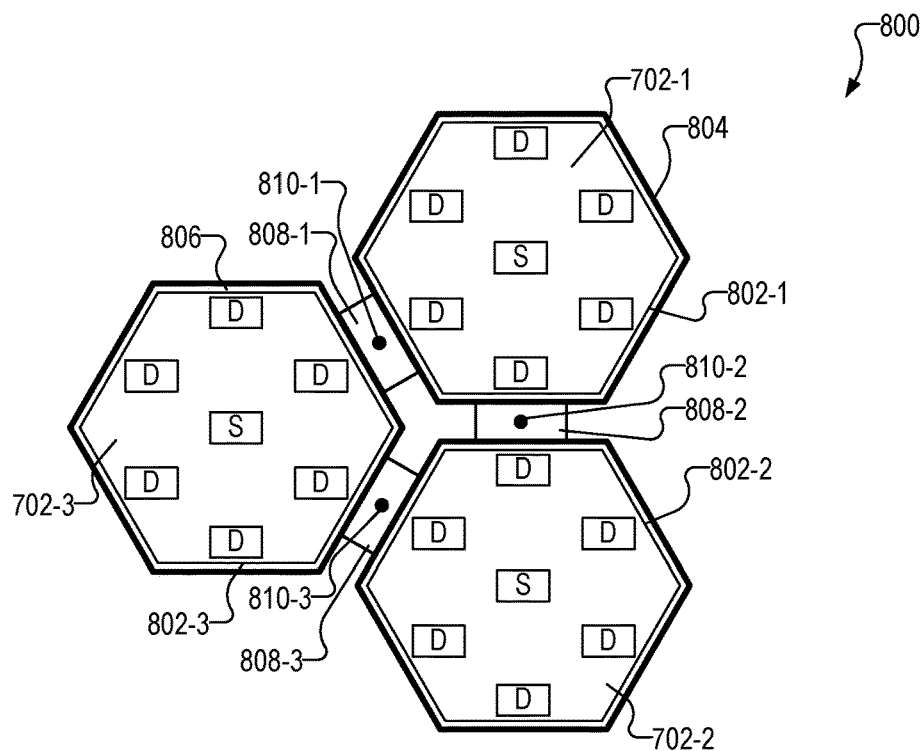
Figure 9:
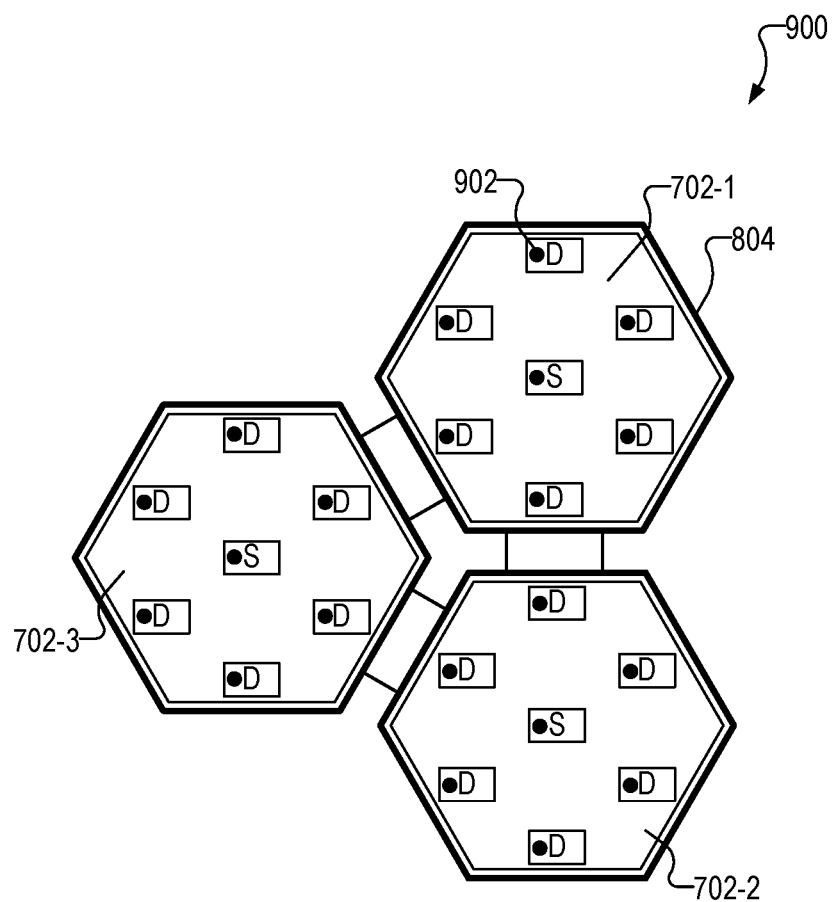

In FIGS. 7-9, the illustrated modules may, in some examples, be physically distinct from each other. For example, as described herein, each module may be configured to be removably attached to a wearable assembly (e.g., by being inserted into a different slot of the wearable assembly). This may allow the modular assemblies to conform to three-dimensional surface geometries, such as a user's head.

In FIGS. 7-9, each illustrated module may include one or more light sources labeled "S" and a set of detectors each labeled "D". Some specific light sources and detectors are also referred to by specific reference numbers.

Each light source depicted in FIGS. 7-9 may be implemented by one or more light sources similar to light source 110 and may be configured to emit light directed at a target (e.g., the brain).

In some examples, each light source may be implemented by dual (e.g., two) light sources that are co-located (e.g., right next to each other within the same module). For example, a module may include a first light source and a second light source. In this configuration, the first light source may emit light having a first wavelength and the second light source may emit light having a second wavelength different than the first wavelength. This dual light source configuration may be used when it is desired for the multimodal measurement system to concurrently measure or detect different properties. For example, pairs of lights sources operating at different wavelengths may be used to measure the concentrations of oxygenated and deoxygenated hemoglobin, which are at different wavelengths.

Each detector depicted in FIGS. 7-9 may implement or be similar to detector 104 and may include a plurality of photodetectors (e.g., SPADs) as well as other circuitry (e.g., TDCs), and may be configured to detect arrival times for photons of the light emitted by one or more light sources after the light is scattered by the target.

FIG. 7 shows an illustrative modular assembly 700 that may implement multimodal measurement system 600. As shown, modular assembly 700 includes a plurality of modules 702 (e.g., modules 702-1 through 702-3). While three modules 702 are shown to be included in modular assembly 700, in alternative configurations, any number of modules 702 (e.g., a single module up to sixteen or more modules) may be included in modular assembly 700. Moreover, while each module 702 has a hexagonal shape, modules 702 may alternatively have any other suitable geometry (e.g., in the shape of a pentagon, octagon, square, rectangular, circular, triangular, free-form, etc.).

Each module 702 includes a light source (e.g., light source 704-1 of module 702-1 and light source 704-2 of module 702-2) and a plurality of detectors (e.g., detectors 706-1 through 706-6 of module 702-1). In the particular implementation shown in FIG. 7, each module 702 includes a single light source and six detectors. Alternatively, each module 702 may have any other number of light sources (e.g., two light sources) and any other number of detectors.

Each light source (e.g., light source 704-1 or light source 704-2) depicted in FIG. 7 may be located at a center region of a surface of the light source's corresponding module. For example, light source 704-1 is located at a center region of a surface 708 of module 702-1. In alternative implementations, a light source of a module may be located away from a center region of the module.

The detectors of a module may be distributed around the light source of the module. For example, detectors 706 of module 702-1 are distributed around light source 704-1 on surface 708 of module 702-1. In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling, etc.) information about the detected signals. Detectors of a module may be alternatively disposed on the module as may serve a particular implementation.

As shown, modular assembly 700 further includes a plurality of electrodes 710 (e.g., electrodes 710-1 through 710-3), which may implement electrodes 608. Electrodes 710 may be located at any suitable location that allows electrodes 710 to be in physical contact with a surface (e.g., the scalp and/or skin) of a body of a user. For example, in modular assembly 700, each electrode 710 is on a module surface configured to face a surface of a user's body when modular assembly 700 is worn by the user. To illustrate, electrode 710-1 is on surface 708 of module 702-1. Moreover, in modular assembly 700, electrodes 710 are located in a center region of each module 702 and surround each module's light source 704. Alternative locations and configurations for electrodes 710 are described herein.

In FIG. 7, modules 702 are shown to be adjacent to and touching one another. Modules 702 may alternatively be spaced apart from one another. For example, FIGS. 8A-8B show another modular assembly 800 that may implement multimodal measurement system 600. In modular assembly 800, modules 702 may be configured to be inserted into individual slots 802 (e.g., slots 802-1 through 802-3, also referred to as cutouts) of a wearable assembly 804. In particular, FIG. 8A shows the individual slots 802 of the wearable assembly 804 before modules 702 have been inserted into respective slots 802, and FIG. 8B shows wearable assembly 804 with individual modules 702 inserted into respective individual slots 802.

Wearable assembly 804 may implement wearable assembly 602 and may be configured as headgear and/or any other type of device configured to be worn by a user.

As shown in FIG. 8A, each slot 802 is surrounded by a wall (e.g., wall 806) such that when modules 702 are inserted into their respective individual slots 802, the walls physically separate modules 702 one from another. In alternative embodiments, a module (e.g., module 702-1) may be in at least partial physical contact with a neighboring module (e.g., module 702-2).

As shown in FIGS. 8A-8B, wearable assembly 804 may include a plurality of connecting structures 808 (e.g., connecting structures 808-1 through 808-3) configured to interconnect each slot 802 of wearable assembly 804. Connecting structures 808 may be implemented by any suitable connecting mechanisms (e.g., ball joints, hinges, elastic bands, etc.) and/or support members (e.g., support frames, bands, rails, etc.). In some examples, connecting structures 808 are flexible and/or movable such that modular assembly 800 may be adjusted to fit a particular body part (e.g., the head). Moreover, with such a configuration, modular assembly 800 can be adjusted to conform to a 3D (non-planar) surface, such as a user's head, and/or to target a specific region of interest (e.g., a specific region of the brain).

As shown in FIGS. 8A-8B, electrodes 810 (e.g., electrodes 810-1 through 810-3) that implement electrodes 608 may be located off-module (i.e., not on any of modules 702) on connecting structures 808. Additionally or alternatively, one or more electrodes may be located off-module on any other structure or component of wearable assembly 804 as may serve a particular implementation.

FIG. 9 shows another modular assembly 900 that may implement multimodal measurement system 600. Modular assembly 900 is similar to modular assembly 800, except that in modular assembly 900, electrodes (e.g., electrode 902) that implement electrodes 608 are on (e.g., integrated into) each of the light sources and detectors of modules 702. The electrodes may be integrated into one or more of sources and detectors of modules 702 in any suitable manner. For example, the light sources and detectors may be implemented by light guides that have distal ends configured to be in contact with a surface of a body of the user. In this example, the electrodes may be integrated into the light guides themselves.

Figure 10:
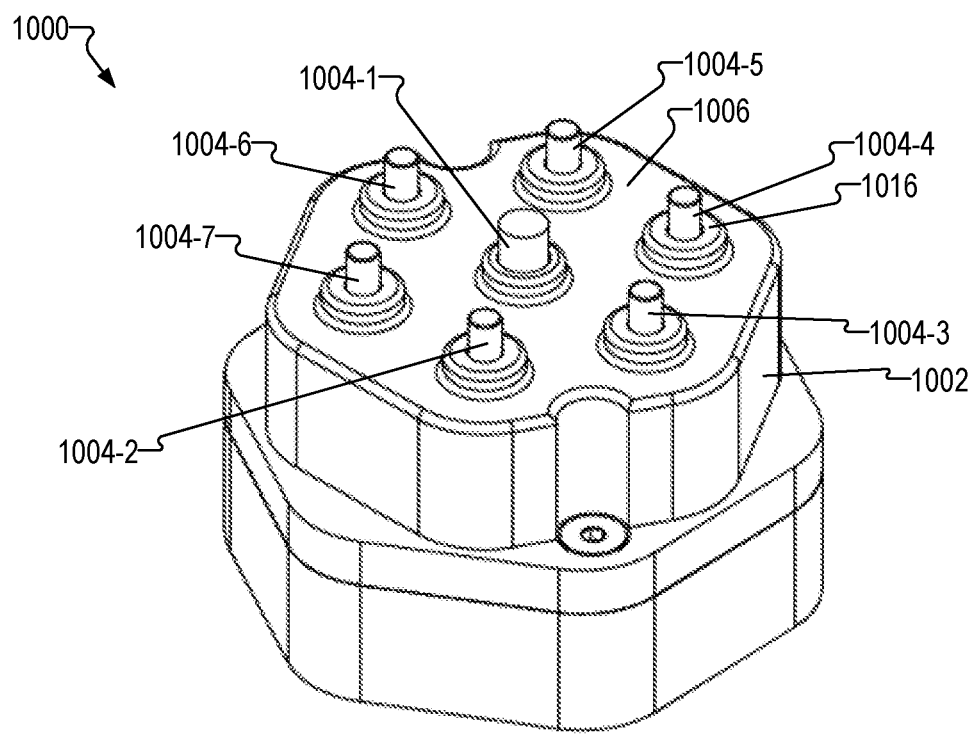
FIG. 10 shows a perspective view of a module.

To illustrate, FIG. 10 shows a perspective view of a module 1000 that may implement any of the modules described herein. Module 1000 is described in more detail in U.S. Provisional Patent Application No. 63/064,688, filed Aug. 12, 2020, the contents of which are incorporated herein by reference in their entirety.

As shown in FIG. 10, module 1000 includes a housing 1002 and a plurality of light guides 1004 (e.g., light guides 1004-1 through 1004-7) protruding from an upper surface 1006 of housing 1002. As used herein with reference to module 1000, "upper" refers to a side of module 1000 that faces a target within a body of a user when module 1000 is worn by the user.

In FIG. 10, light guide 1004-1 is part of a light source assembly included in module 1000. As such, light may pass through light guide 1004-1 towards the target while module 1000 is being worn by the user. Light guides 1004-2 through 1004-7 are parts of detector assemblies included in module 1000. As such, light may be received by light guides 1004-2 through 1004-7 after the light is scattered by the target.

In some examples, a least a portion of light guides 1004 are made out of a conductive material, which allows light guides 1004 themselves to function as the electrodes that implement electrodes 608.

Figure 11:
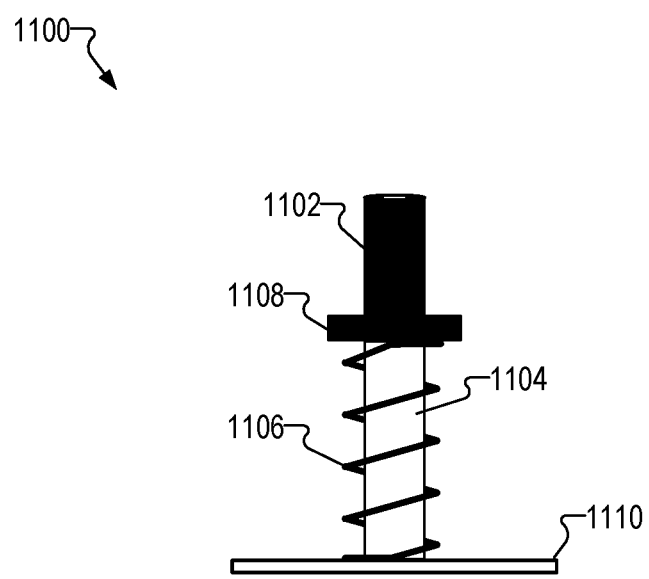
FIG. 11 shows an exemplary light guide assembly.

To illustrate, FIG. 11 shows an exemplary light guide assembly 1100 that may implement any of the light guides 1004 shown in FIG. 10. As shown, light guide assembly 1100 includes an upper light guide portion 1102, a lower light guide portion 1104, a spring member 1106, and a flange 1108 in between upper and lower light guide portions 1102 and 1104. FIG. 11 also depicts a printed circuit board (PCB) 1110 attached to a proximal end of lower light guide portion 1104.

In some examples, lower light guide portion 1104, spring member 1106, flange 1108, and PCB 1110 are configured to be housed within housing 1002 of module 1000, while upper light guide portion 1102 is configured to protrude from upper surface 1006 of housing 1002. In this configuration, upper light guide portion 1102 may be in contact with a surface of a user.

In the example of FIG. 11, upper light guide portion 1102 and flange 1008 are made out of a conductive material, which allows a distal end of the upper light guide portion 1102 to function as an electrode that may be used to detect electrical activity within the a target. This conductive portion may be conductively coupled to spring member 1106, which is also conductive. In this manner, spring member 1106 may conductively couple the conductive portion of upper light guide portion 1102 with circuitry included on PCB 1110. The circuitry may be configured to process the electrical activity detected by the electrode implemented by the conductive upper light guide portion 1102 in any of the ways described herein.

In some alternative example, both upper and lower light guide portions 1102 and 1104 are made out of the conductive material.

As shown, spring member 1106 comprises a coil spring positioned around an external surface of lower light guide portion 1104. A proximal end of spring member 1106 pushes against PCB 1110 (or any other suitable support structure), while the distal end of spring member 1106 pushes against flange 1108. Flange 1108 may be any suitable structure (e.g., a ring) attached to or protruding from upper light guide portion 1102 and/or lower light guide portion 1104. By pressing against flange 1108, spring member 1106 pushes the distal end of upper light guide portion 1102 away from upper surface 1006 of housing 1002 (shown in FIG. 10). In this manner, the distal end of upper light guide portion 1102 may be biased away from upper surface 1006 of housing 1002 and toward the user's body.

Figure 12A:
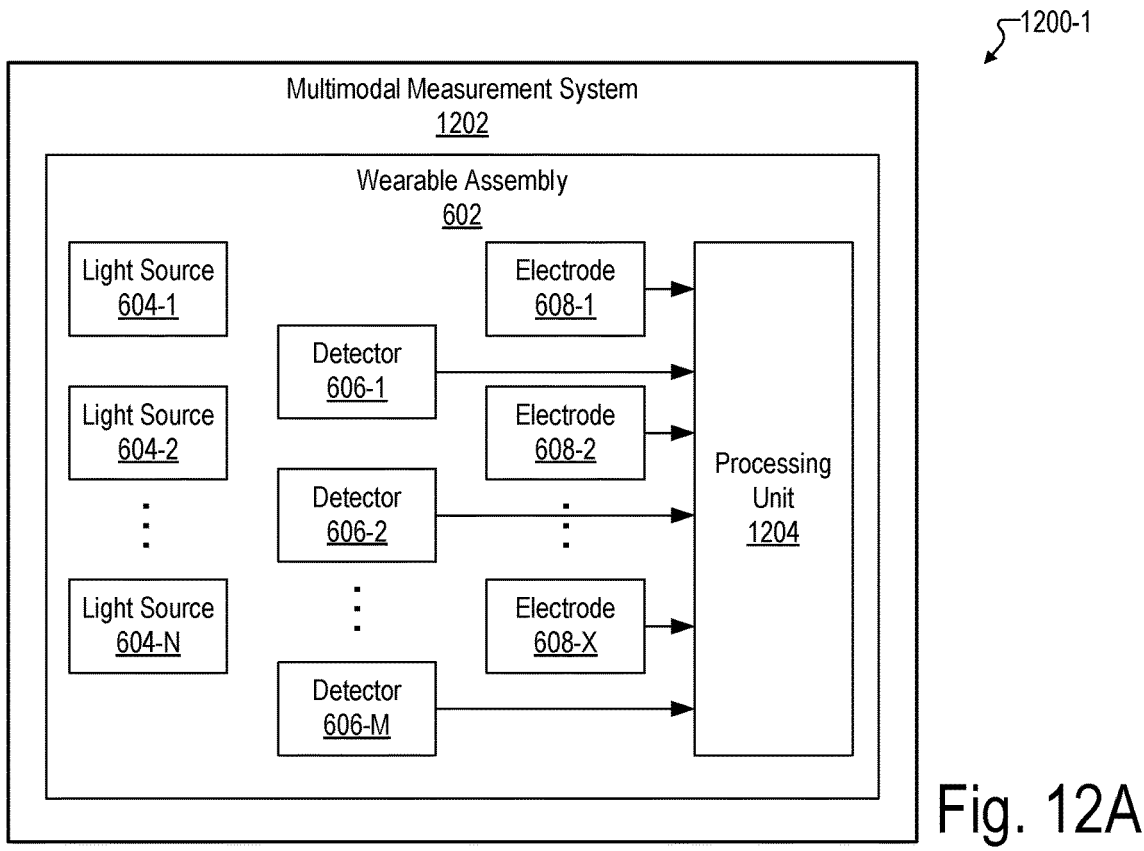
FIGS. 12A-12B show illustrative configurations of an exemplary multimodal measurement system.
Figure 12B:
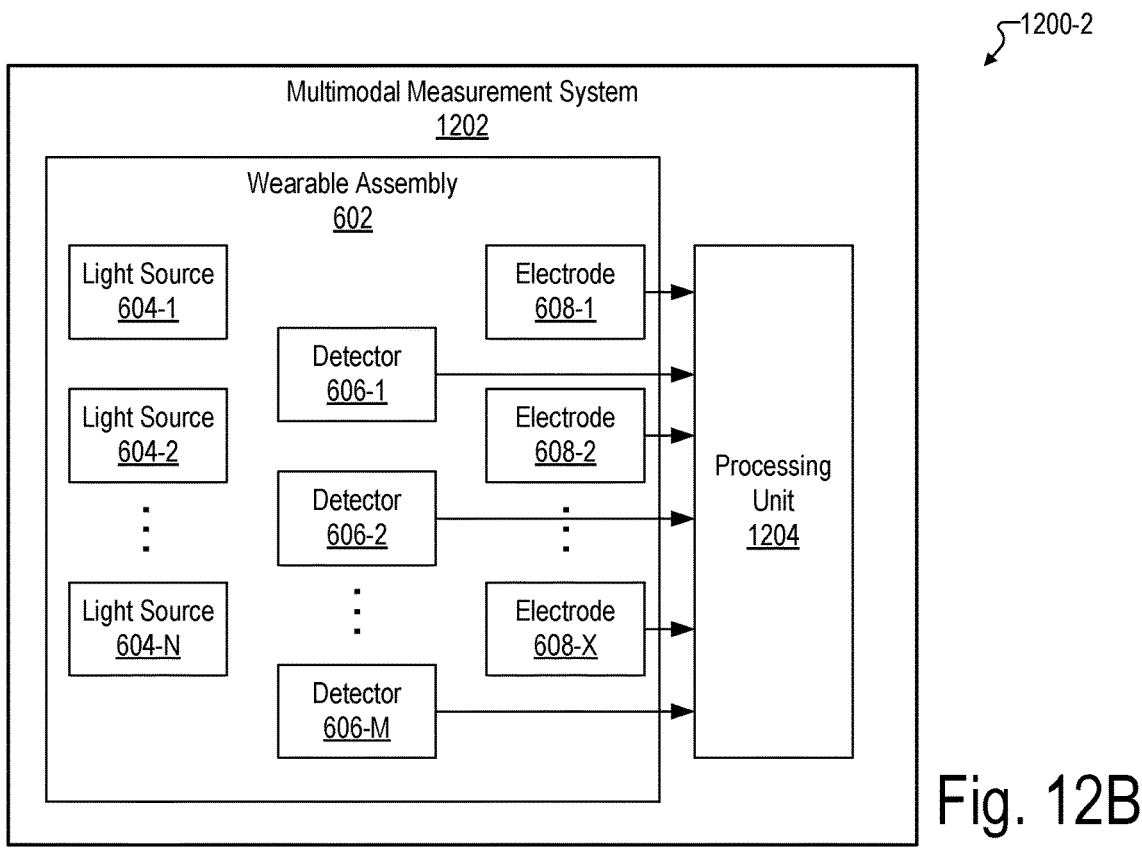

In some examples, the multimodal measurement systems described herein may further include a processing unit configured to perform one or more operations based on photon arrival times detected by the detectors described herein and the electrical activity detected by the electrodes described herein. For example, FIGS. 12A-12B show illustrative configurations 1200-1 and 1200-2 of an exemplary multimodal measurement system 1202 in accordance with the principles described herein.

Multimodal measurement system 1202 may be an implementation of multimodal measurement system 600 and, as shown, includes the wearable assembly 602, light sources 604, detectors 606, and electrodes 608 described in connection with FIG. 6.

In configuration 1200-1, a processing unit 1204 is also included in wearable assembly 602. In configuration 1200-2, processing unit 1204 is not included in wearable assembly 602 (i.e., processing unit 1204 is located external to wearable assembly 602). Either configuration 1200-1 or 1200-2 may be used in accordance with the systems, circuits, and methods described herein.

In configuration 1200-2, processing unit 1204 is not included in wearable assembly 602. For example, processing unit 1204 may be included in a wearable device separate from wearable assembly 602. To illustrate, processing unit 1204 may be included in a wearable device configured to be worn off the head (e.g., on a belt) while wearable assembly 602 is worn on the head. In these examples, one or more communication interfaces (e.g., cables, wireless interfaces, etc.) may be used to facilitate communication between wearable assembly 602 and the separate wearable device.

Additionally or alternatively, in configuration 1200-2, processing unit 1204 may be remote from the user (i.e., not worn by the user). For example, processing unit 1204 may be implemented by a stand-alone computing device communicatively coupled to wearable assembly 602 by way of one or more communication interfaces (e.g., cables, wireless interfaces, etc.).

In some examples, processing unit 1204 may be distributed between multiple devices and/or multiple locations as may serve a particular implementation. Processing unit 1204 may be implemented by processor 108, controller 112, control circuit 204, and/or any other suitable processing and/or computing device or circuit.

Figure 13:
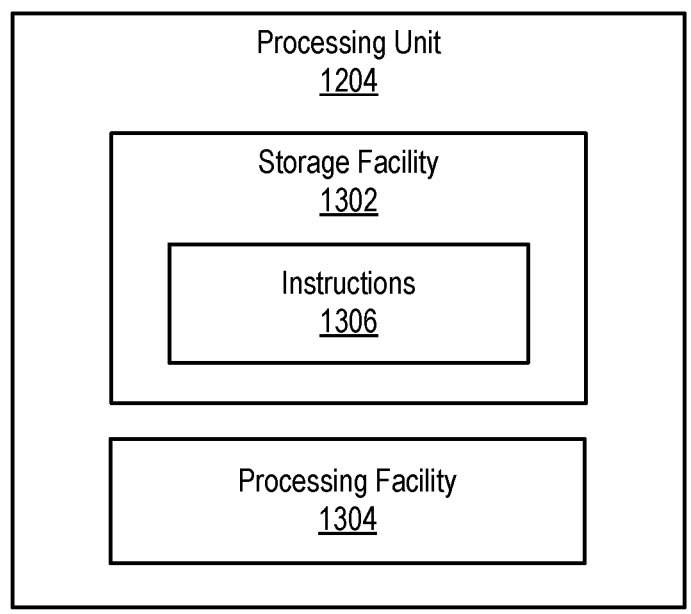
FIG. 13 illustrates an exemplary processing unit.

For example, FIG. 13 illustrates an exemplary implementation of processing unit 1204 in which processing unit 1204 includes a memory (storage facility) 1302 and a processor (processing facility) 1304 configured to be selectively and communicatively coupled to one another. In some examples, memory 1302 and processor 1304 may be distributed between multiple devices and/or multiple locations as may serve a particular implementation.

Memory 1302 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1302 may maintain (e.g., store) executable data used by processor 1304 to perform one or more of the operations described herein. For example, memory 1302 may store instructions 1306 that may be executed by processor 1304 to perform any of the operations described herein. Instructions 1306 may be implemented by any suitable application, program (e.g., sound processing program), software, code, and/or other executable data instance. Memory 1302 may also maintain any data received, generated, managed, used, and/or transmitted by processor 1304.

Processor 1304 may be configured to perform (e.g., execute instructions 1306 stored in memory 1302 to perform) various operations described herein. For example, processor 1304 may be configured to perform any of the operations described herein as being performed by processing unit 1204.

Processing unit 1204 may be configured to generate optical measurement data (e.g., fNIRS data) based on the arrival times detected by detectors 606 and electrical measurement data (e.g., EEG data) based on the electrical activity detected by electrodes 608. This may be performed in any suitable manner.

For example, processing unit 1204 may be configured to process the optical measurement data and the electrical measurement data in accordance with a data fusion heuristic to generate an estimate of cortical source activity. In some examples, this may be performed in real-time while detectors 606 are detecting the arrival times and electrodes 608 are detecting the electrical activity.

To illustrate, an exemplary data fusion heuristic that may be employed by processing unit 1204 with respect to fNIRS and EEG data will now be described. The operations described herein assimilate samples of each modality as they become available and update the current estimates of cortical source activity in real time.

For the observation equation of the EEG, a standard linear propagation model may be represented by the following equation.

$$v_k = L s_k + n_k \quad (1)$$

In equation 1, $v_k$ is a vector of voltages collected in the EEG sensors at instant k, L is the so-called lead field matrix that describes the propagation of electrical activity generated by sources in the cortex to the sensors, and $s_k$ is the amplitude of the current source density in different parts of the cortex at sample time k, and $n_k$ is a sensor noise vector. The lead field matrix can be precomputed based on a model of the head derived from magnetic resonance imaging (MRI) data or an established atlas. For the observation equation of fNIRS, the following linearized model may be used.

$$f_k = J a_k + m_k \quad (2)$$

In equation 2, $f_k$ is a sample of oxy and deoxy absorption, J=MS, factorizes into the product of the MBLL linear transformation and sensitivity matrix S, $a_k$ is a vector of light absorption on each location of the source space, and $m_k$ is optical sensor noise. The matrices M and S can be precomputed. To link the light absorption signal $a_k$ with the cortical electrical activity $s_k$ in a computationally tractable manner, the following convolution model may be used.

$$a_k = \sum_{i=0}^{n} h_i s_{k-i} \quad (3)$$

In equation 3, the $h_i$ coefficients represent a low-pass FIR filter. Utilizing this approach allows for a fusion of EEG and fNIRS data that provides a method to link delay and strength of activation between the two modalities.

The data fusion heuristic described herein addresses at least two problems: 1) estimation of the vector time series of source activation $s_k$ from the time series of sensor data $v_k$ and $f_k$, and 2) estimation of the filter coefficients $h_i$ from the source time series $s_k$ and $a_k$.

To address the first problem, equation 3 is plugged into equation 2 yielding:

$$f_k = J\left(\sum_{i}^{n} h_i s_{k-i}\right) + m_k \quad (4)$$

$$f_k = J h_1 s_k + \underbrace{\left(\sum_{i=1}^{n} h_i s_{k-i}\right)}_{S_{k-1}} + m_k$$

In equation 4, $S_{k-1}$ is the low-pass filtered version of the source time series up to the k−1 sample and can be considered fixed and known at the moment of estimating the $s_k$ source vector. Equation 4 may be used to rewrite equations 1 and 2 in a more compact way as follows:

$$\begin{bmatrix} v_k \\ f_k \end{bmatrix} = \begin{bmatrix} L \\ J \end{bmatrix} s_k + \begin{bmatrix} 0 \\ J \end{bmatrix} S_{k-1} + \begin{bmatrix} n_k \\ m_k \end{bmatrix} \quad (5)$$

Equation 5 is an ill-posed system because there are many more unknown sources than sensors. Hence, it may be solved for $s_k$ using a penalized least squares algorithm. To solve the second problem, equation 3 is rewritten in matrix form as follows.

$$A_k = Sh \quad (6)$$

In equation 6, $A_k = [a_k, \ldots, a_{k-N}]$ is a segment of light absorption signal and S is an embedding of past s source electrical activity. Equation 6 may be solved using least squares linear regression or any other suitable technique.

FIGS. 14-19 illustrate embodiments of a wearable device 1400 that includes elements of the multimodal detection systems described herein. In particular, the wearable devices 1400 shown in FIGS. 14-19 include a plurality of modules 1402, similar to any of the modules and module configurations described herein. For example, each module 1402 may include a light source, a plurality of detectors, and one or more electrodes. The wearable devices 1400 may each also include a controller (e.g., controller 112) and a processor (e.g., processor 108) and/or be communicatively connected to a controller and processor. In general, wearable device 1400 may be implemented by any suitable headgear and/or clothing article configured to be worn by a user. The headgear and/or clothing article may include batteries, cables, and/or other peripherals for the components of the multimodal measurement systems described herein.

Figure 14:
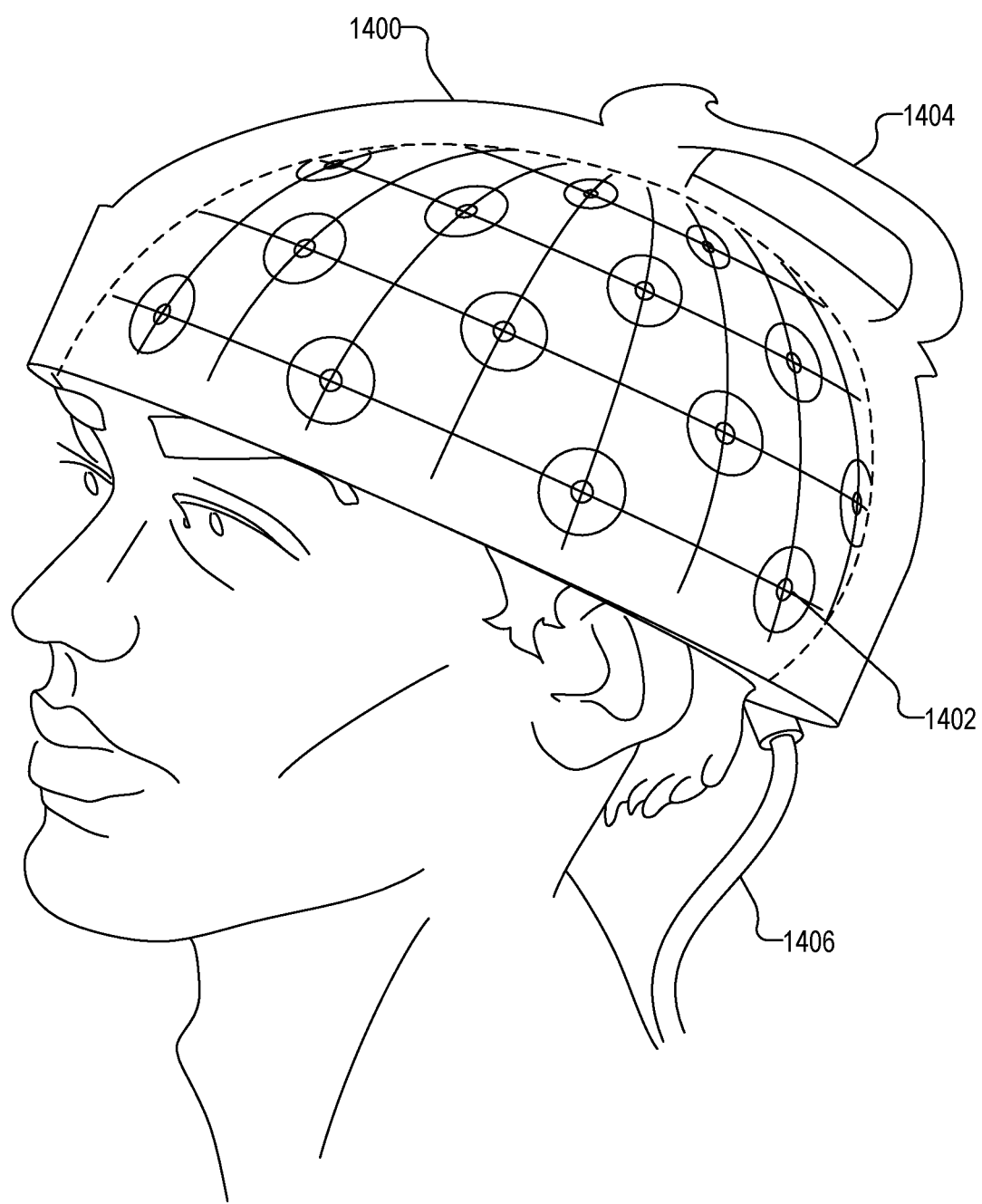
FIGS. 14-19 illustrate embodiments of a wearable device that includes elements of the optical detection systems described herein.
Figure 15:
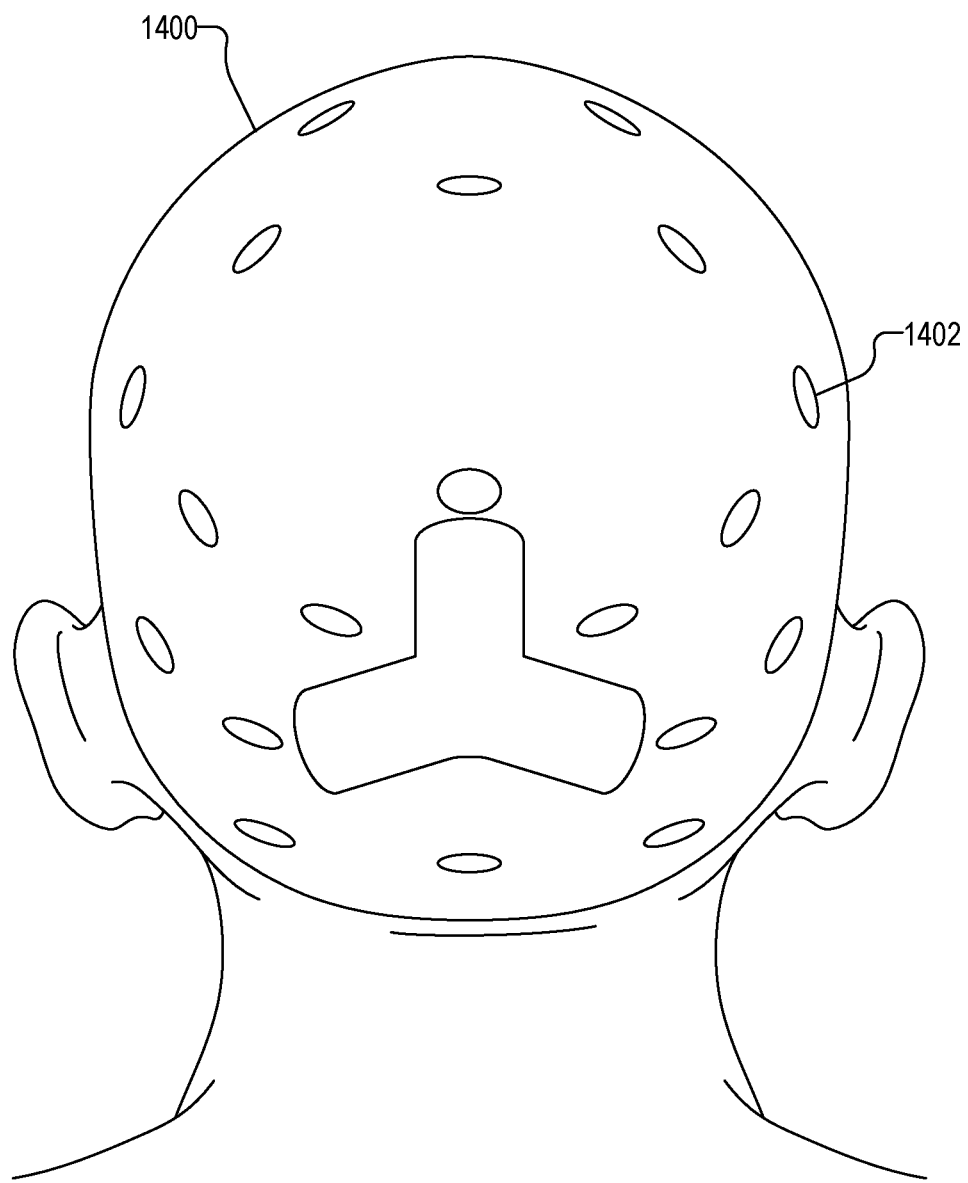
Figure 16:
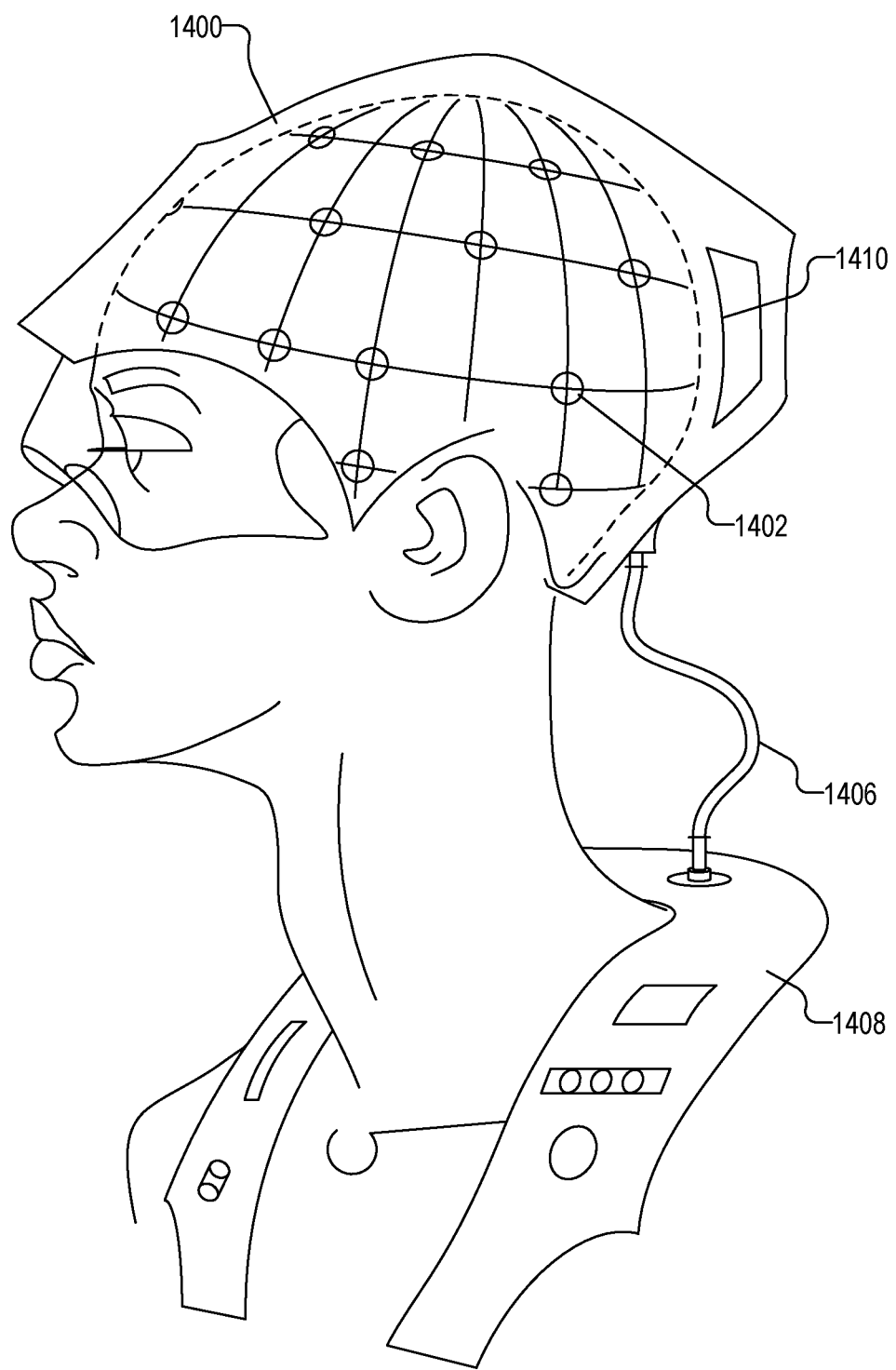

FIG. 14 illustrates an embodiment of a wearable device 1400 in the form of a helmet with a handle 1404. A cable 1406 extends from the wearable device 1400 for attachment to a battery or hub (with components such as a processor or the like). FIG. 15 illustrates another embodiment of a wearable device 1400 in the form of a helmet showing a back view. FIG. 16 illustrates a third embodiment of a wearable device 1400 in the form of a helmet with the cable 1406 leading to a wearable garment 1408 (such as a vest or partial vest) that can include a battery or a hub. Alternatively or additionally, the wearable device 1400 can include a crest 1410 or other protrusion for placement of the hub or battery.

Figure 17:
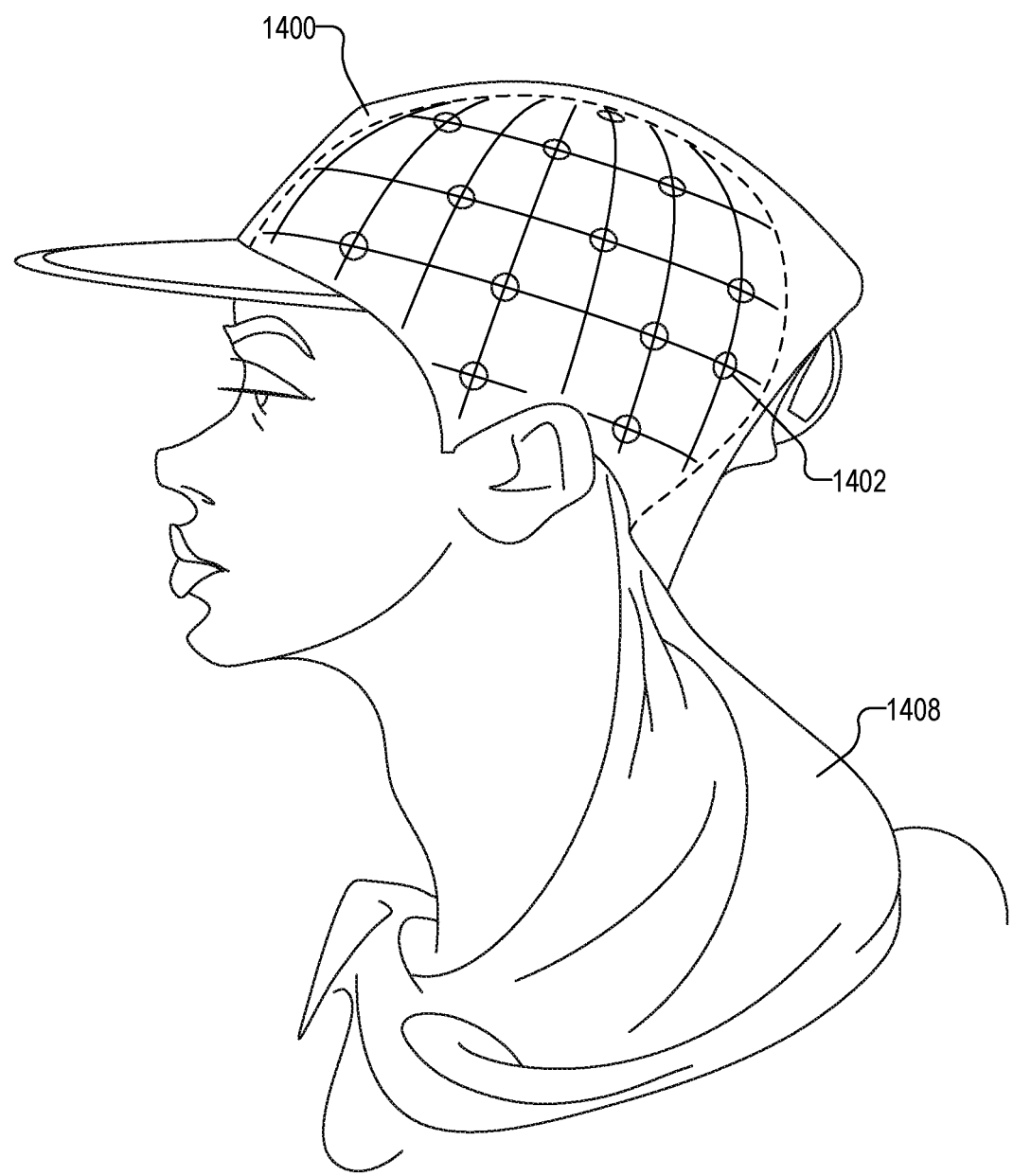
Figure 18:
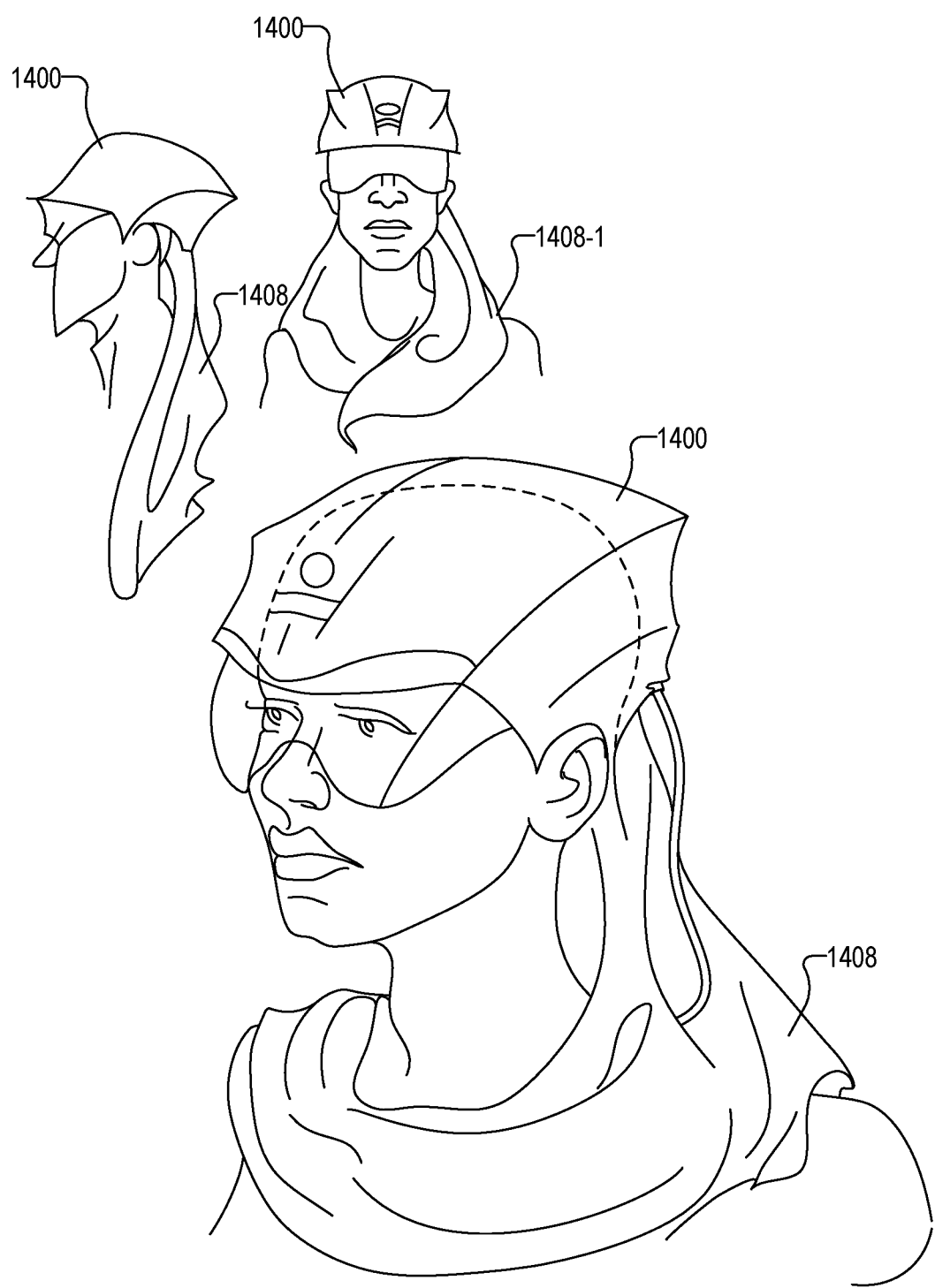

FIG. 17 illustrates another embodiment of a wearable device 1400 in the form of a cap with a wearable garment 1408 in the form of a scarf that may contain or conceal a cable, battery, and/or hub. FIG. 18 illustrates additional embodiments of a wearable device 1400 in the form of a helmet with a one-piece scarf 1408 or two-piece scarf

Figure 19:
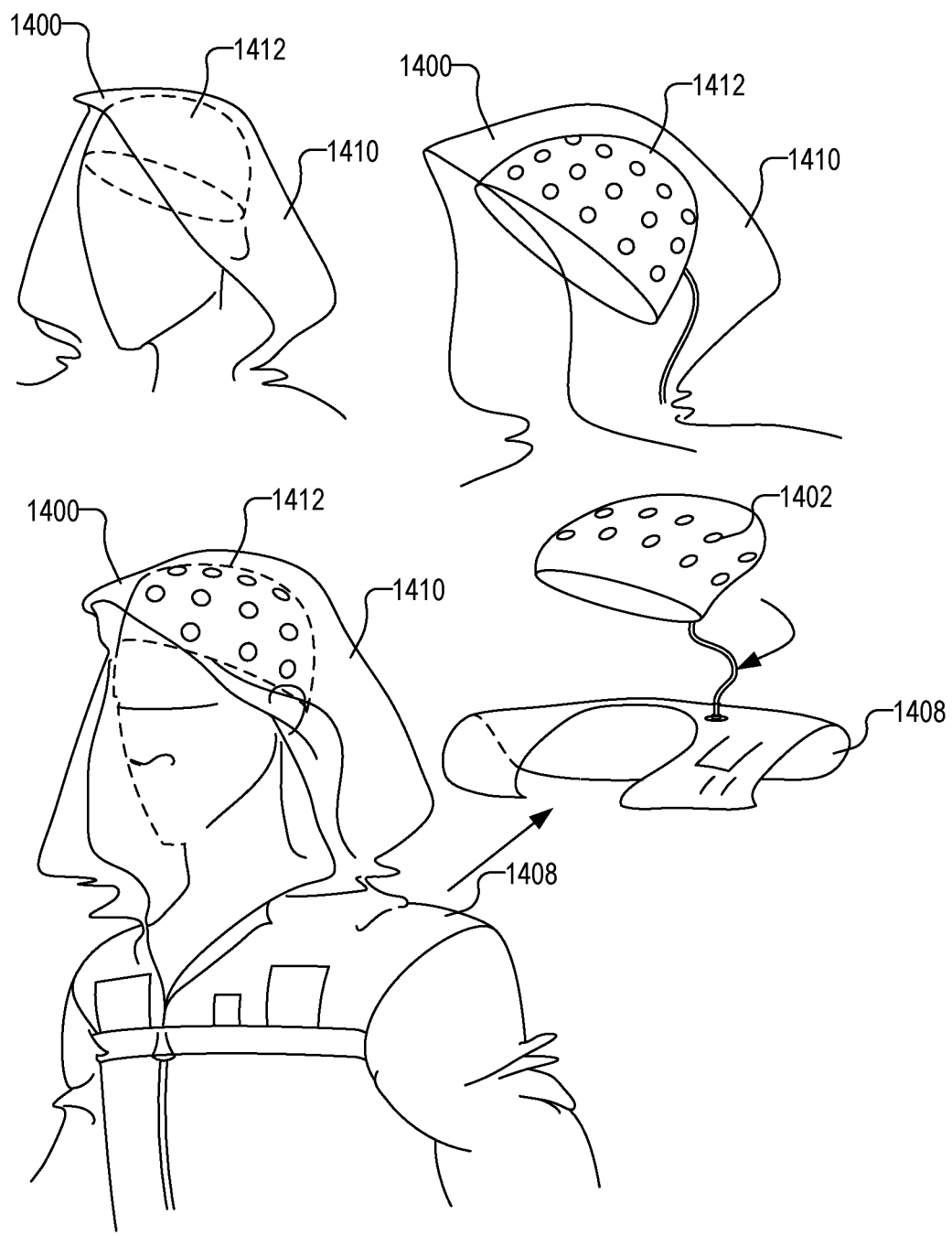

1408-1. FIG. 19 illustrates an embodiment of a wearable device 1400 that includes a hood 1410 and a beanie 1412 which contains the modules 1402, as well as a wearable garment 1408 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 20:
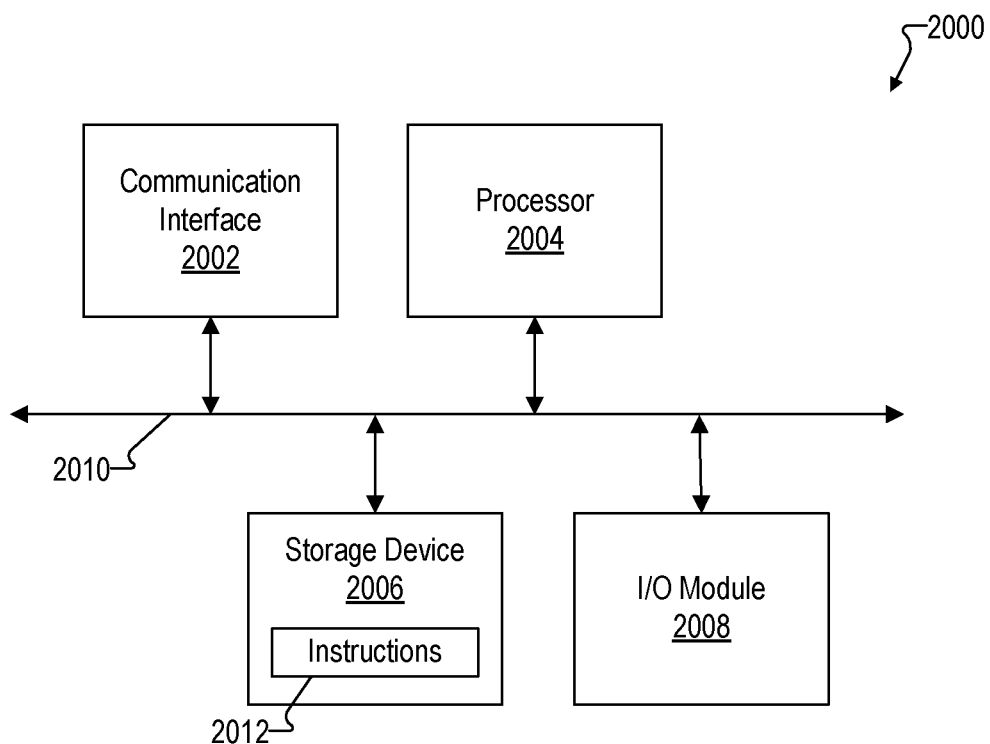
FIG. 20 illustrates an exemplary computing device.

FIG. 20 illustrates an exemplary computing device 2000 that may be specifically configured to perform one or more of the processes described herein. Any of the systems, units, computing devices, and/or other components described herein may be implemented by computing device 2000.

As shown in FIG. 20, computing device 2000 may include a communication interface 2002, a processor 2004, a storage device 2006, and an input/output ("I/O") module 2008 communicatively connected one to another via a communication infrastructure 2010. While an exemplary computing device 2000 is shown in FIG. 20, the components illustrated in FIG. 20 are not intended to be limiting. Additional or alternative components may be used in other embodiments. Components of computing device 2000 shown in FIG. 20 will now be described in additional detail.

Communication interface 2002 may be configured to communicate with one or more computing devices. Examples of communication interface 2002 include, without limitation, a wired network interface (such as a network interface card), a wireless network interface (such as a wireless network interface card), a modem, an audio/video connection, and any other suitable interface.

Processor 2004 generally represents any type or form of processing unit capable of processing data and/or interpreting, executing, and/or directing execution of one or more of the instructions, processes, and/or operations described herein. Processor 2004 may perform operations by executing computer-executable instructions 2012 (e.g., an application, software, code, and/or other executable data instance) stored in storage device 2006.

Storage device 2006 may include one or more data storage media, devices, or configurations and may employ any type, form, and combination of data storage media and/or device. For example, storage device 2006 may include, but is not limited to, any combination of the non-volatile media and/or volatile media described herein. Electronic data, including data described herein, may be temporarily and/or permanently stored in storage device 2006. For example, data representative of computer-executable instructions 2012 configured to direct processor 2004 to perform any of the operations described herein may be stored within storage device 2006. In some examples, data may be arranged in one or more databases residing within storage device 2006.

I/O module 2008 may include one or more I/O modules configured to receive user input and provide user output. I/O module 2008 may include any hardware, firmware, software, or combination thereof supportive of input and output capabilities. For example, I/O module 2008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2008 is configured to provide graphical data to a display for presentation to a user. The graphical data may be representative of one or more graphical user interfaces and/or any other graphical content as may serve a particular implementation.

Figure 21:
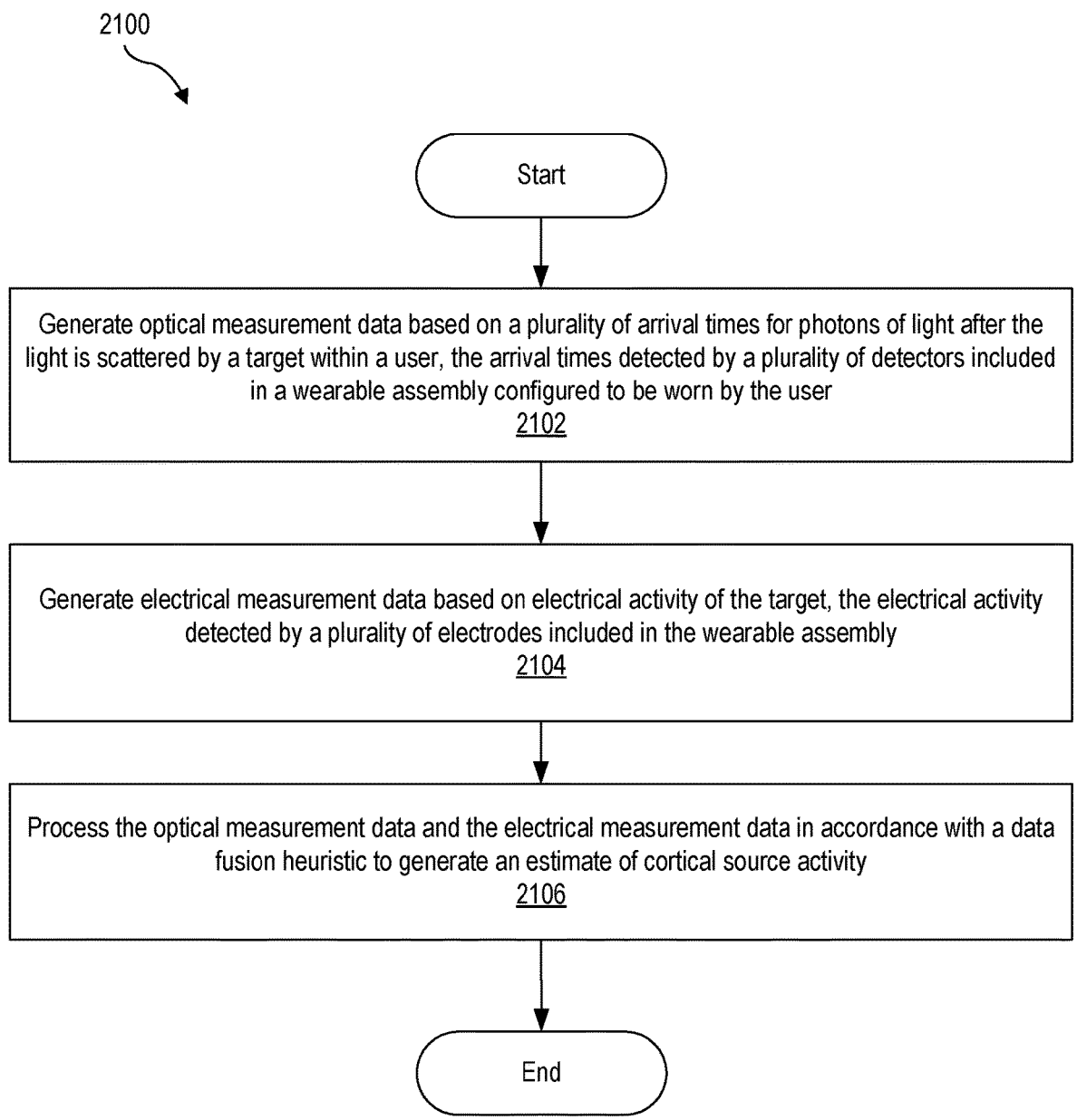
FIG. 21 illustrates an exemplary method.

FIG. 21 illustrates an exemplary method 2100 that may be performed by processing unit 1204 and/or any implementation thereof. While FIG. 21 illustrates exemplary operations according to one embodiment, other embodiments may omit, add to, reorder, and/or modify any of the operations shown in FIG. 21. Each of the operations shown in FIG. 21 may be performed in any of the ways described herein.

At operation 2102, a processing unit generates optical measurement data based on a plurality of arrival times for photons of light after the light is scattered by a target within a user, the arrival times detected by a plurality of detectors included in a wearable assembly configured to be worn by the user.

At operation 2104, the processing unit generates electrical measurement data based on electrical activity of the target, the electrical activity detected by a plurality of electrodes included in the wearable assembly.

At operation 2106, the processing unit processes the optical measurement data and the electrical measurement data in accordance with a data fusion heuristic to generate an estimate of cortical source activity.

An illustrative multimodal measurement system includes a wearable assembly configured to be worn by a user and comprising: a plurality of light sources each configured to emit light directed at a target within the user, a plurality of detectors configured to detect arrival times for photons of the light after the light is scattered by the target, and a plurality of electrodes configured to be external to the user and detect electrical activity of the target.

Another illustrative multimodal measurement system includes a wearable assembly configured to be worn by a user and comprising: a light source configured to emit light directed at a target within the user, a detector configured to detect arrival times for photons of the light after the light is scattered by the target, and an electrode configured to be external to the user and detect electrical activity of the target.

Another illustrative multimodal measurement system includes a headgear configured to be worn on a head of a user and having a plurality of slots; a first module configured to be located in a first slot of the plurality of slots and comprising: a first light source configured to emit light directed at a target within the head of the user, and a first set of detectors configured to detect arrival times for photons of the light emitted by the first light source; a second module configured to be located in a second slot of the plurality of slots and comprising: a second light source configured to emit light directed at the target within the head of the user, and a second set of detectors configured to detect arrival times for photons of the light emitted by the second light source; and a plurality of electrodes on one or more of the headgear, the first module, or the second module and configured to detect electrical activity of the target.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A multimodal measurement system comprising:
   a wearable assembly configured to be worn by a user; and
   a module configured to be removably inserted into the wearable assembly and comprising:
      a housing,
      a printed circuit board (PCB) housed within the housing, and
      a light guide assembly configured to emit light directed at a target within the user, the light guide assembly comprising:
         a lower light guide portion housed within the housing and having a proximal end attached to the PCB,
         a conductive spring member housed within the housing and comprising a coil positioned around an external surface of the lower light guide portion, and
         a conductive upper light guide portion connected to the lower light guide portion and configured to protrude from an upper surface of the housing and be in contact with a surface of a body of the user, the conductive upper light guide portion conductively coupled to circuitry on the PCB by way of the conductive spring member and configured to function as an electrode that detects electrical activity of the target.

2. The multimodal measurement system of claim 1, wherein the module further comprises a set of detectors configured to detect arrival times for photons of the light after the light is scattered by the target.

3. The multimodal measurement system of claim 2, further comprising a processing unit configured to generate optical measurement data based on the arrival times detected by the set of detectors and electrical measurement data based on the electrical activity detected by the conductive upper light guide portion configured to function as the electrode.

4. The multimodal measurement system of claim 3, wherein the optical measurement data comprises time-domain functional near infrared spectroscopy (fNIRS) data and the electrical measurement data comprises electroencephalogram (EEG) data.

5. The multimodal measurement system of claim 3, wherein the processing unit is further configured to process the optical measurement data and the electrical measurement data in accordance with a data fusion heuristic to generate an estimate of cortical source activity.

6. The multimodal measurement system of claim 5, wherein the generating of the estimate of the cortical source activity is performed in real-time while the set of detectors is detecting the arrival times and the conductive upper light guide portion configured to function as the electrode is detecting the electrical activity.

7. The multimodal measurement system of claim 3, wherein the processing unit is included in the wearable assembly.

8. The multimodal measurement system of claim 3, wherein the processing unit is not included in the wearable assembly.

9. The multimodal measurement system of claim 1, wherein the wearable assembly comprises a slot surrounded by a wall, and wherein the module is configured to be removably inserted into the slot.

10. The multimodal measurement system of claim 1, further comprising:
    an additional module configured to be removably inserted into the wearable assembly and comprising an additional light guide assembly configured to emit additional light directed at the target.

11. The multimodal measurement system of claim 10, wherein the additional module further comprises an additional set of detectors configured to detect arrival times for photons of the additional light after the additional light is scattered by the target.

12. The multimodal measurement system of claim 10, wherein the additional light guide assembly comprises an additional conductive upper light guide portion configured to function as an electrode that detects the electrical activity of the target.

13. The multimodal measurement system of claim 10, wherein the additional light emitted by the additional light guide assembly has a wavelength different than a wavelength of the light emitted by the light guide assembly.

14. The multimodal measurement system of claim 1, further comprising an electrode on a surface of the module.

15. The multimodal measurement system of claim 1, wherein the conductive upper light guide portion configured to function as the electrode is conductively isolated from a remaining number of electrodes of the multimodal measurement system to create at least two channels.

16. The multimodal measurement system of claim 1, wherein the electrical activity comprises electroencephalogram (EEG) activity.

* * * * *